US 6,592,303 B2
United States Patent
Kataoka et al.
(10) Patent No.: US 6,592,303 B2
(45) Date of Patent: Jul. 15, 2003

(54) THROW-AWAY TIP

(75) Inventors: Hideaki Kataoka, Kyoto (JP); Ayumu Torimoto, Kyoto (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 09/942,059

(22) Filed: Aug. 28, 2001

(65) Prior Publication Data

US 2002/0054793 A1 May 9, 2002

(30) Foreign Application Priority Data

| Aug. 30, 2000 | (JP) | 2000-261739 |
| Aug. 30, 2000 | (JP) | 2000-261740 |
| Aug. 30, 2000 | (JP) | 2000-261741 |
| Oct. 27, 2000 | (JP) | 2000-329625 |

(51) Int. Cl.$^7$ .................. B23B 27/00; B23B 29/00
(52) U.S. Cl. ....................... 407/113; 407/118
(58) Field of Search .................. 407/118, 119, 407/120, 115, 116, 113, 114, 173; 408/5, 6, 11, 134; 82/1.11, 118, 120, 173

(56) References Cited

U.S. PATENT DOCUMENTS

| 4,471,444 A | * | 9/1984 | Yee et al. ................. 700/175 |
| 4,593,277 A | * | 6/1986 | Langan ........................ 340/679 |
| 4,885,530 A | * | 12/1989 | Mayer et al. ............... 324/658 |
| 4,927,300 A | * | 5/1990 | Ramalingam et al. ...... 407/120 |
| 5,000,036 A | * | 3/1991 | Yellowley et al. ............ 73/104 |
| 5,176,053 A | * | 1/1993 | Alvelid et al. .............. 374/141 |
| 5,777,231 A | * | 7/1998 | Patel et al. ................... 73/629 |

FOREIGN PATENT DOCUMENTS

| EP | 0-685297 | 5/1994 |
| EP | 1-095732 | 5/2001 |
| JP | 3-120323 | 12/1991 |
| JP | 9-038846 | 2/1997 |
| WO | 90/05607 | 5/1990 |

* cited by examiner

Primary Examiner—Willmon Fridie, Jr.
(74) Attorney, Agent, or Firm—Hogan & Hartson, LLP

(57) ABSTRACT

A throw-away tip 1 of the present invention has a rake face 5 formed on a surface of a base 2 and a flank 8 intersecting with the rake face 5. The intersection ridge between the rake face 5 and flank 8 defines a cutting edge 9. A sensor line 12 is made out of a conductive film extending along the cutting edge 9 and having a predetermined width. The sensor line 12 is provided in an electrically insulative relation with respect to the base 2. According to the present invention, one side edge L of the sensor line 12 is provided on the flank 8 substantially in parallel with the intersection ridge, while the other side edge U of the sensor line 12 is provided on the rake face 5 side from the intersection ridge.

13 Claims, 17 Drawing Sheets

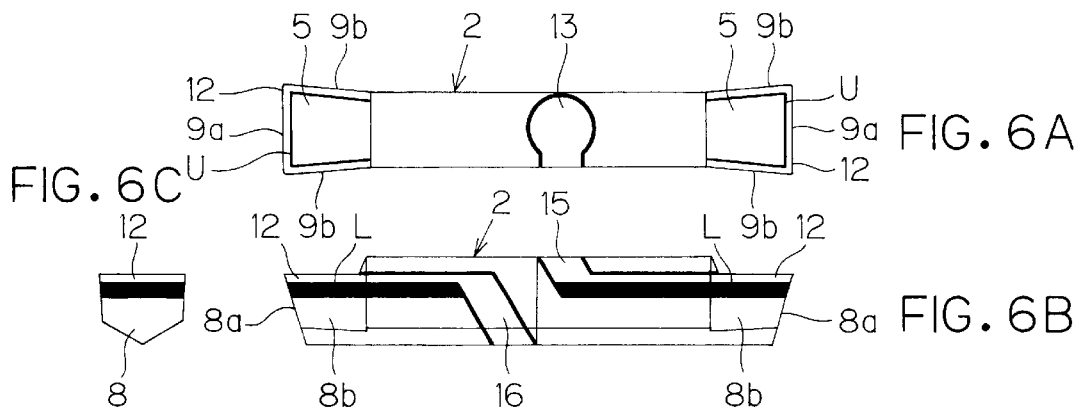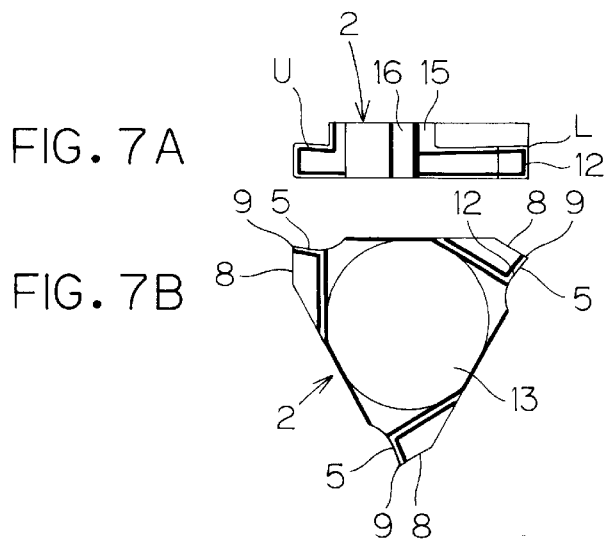

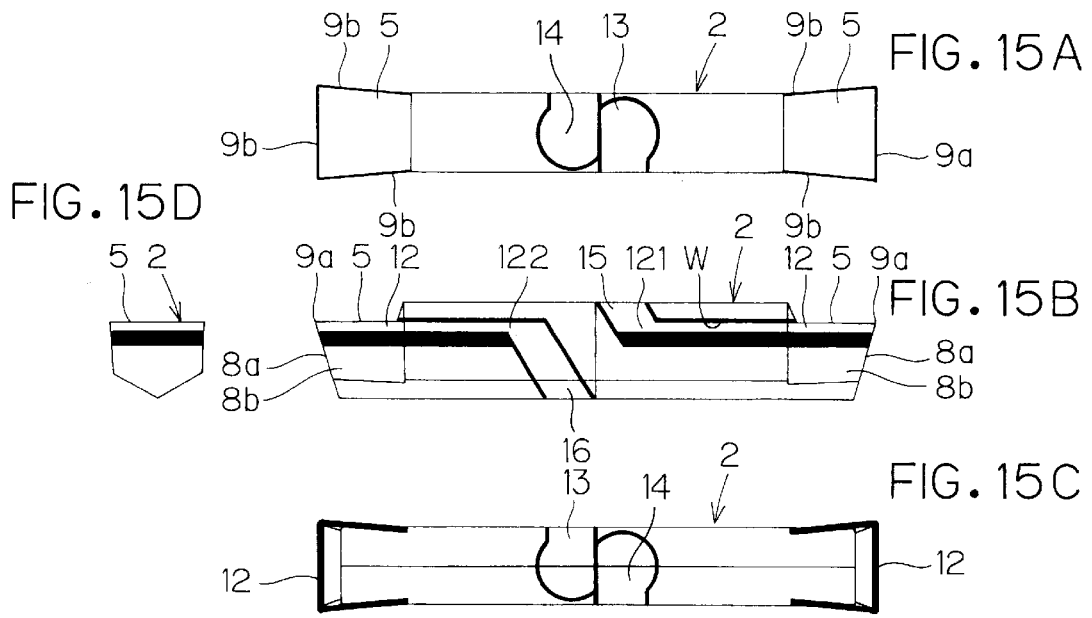
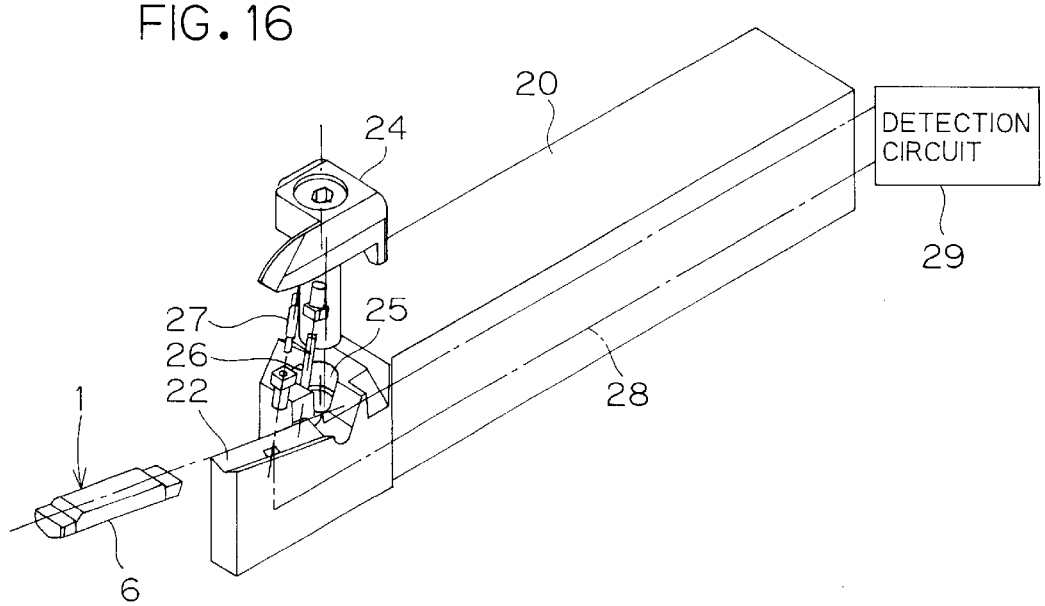

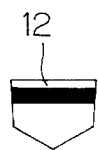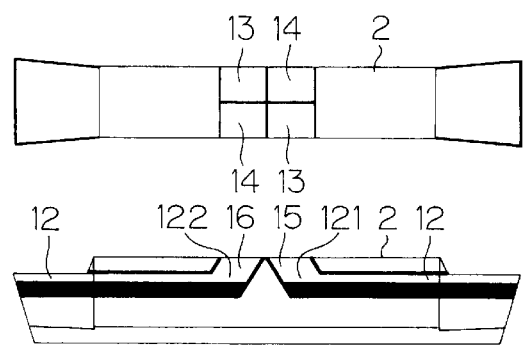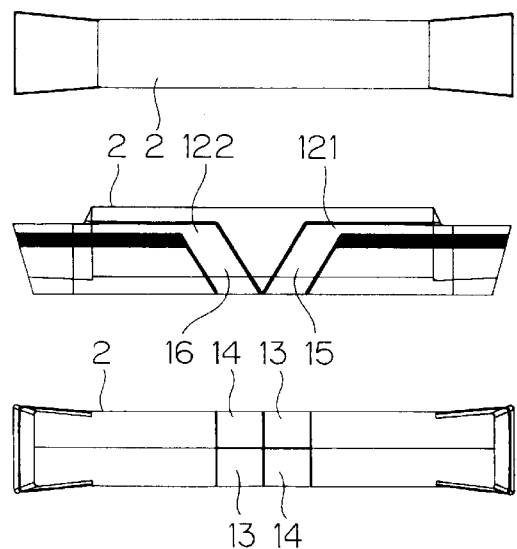

THROW-AWAY TIP

This application is based on application Nos. 2000-261740, 2000-261741, 2000-261739 and 2000-329625 filed in Japan, the contents of which are incorporated herein by reference.

BACKGROUND OF THE INVENTION

1. Field of the Invention

The present invention relates to a throw-away tip for use in a cutting process, more specifically, it relates to a throw-away tip providing a sensor line for finding wearing down of an edge.

2. Description of Related Art

Throw-away tips are known which are adapted to be attached to a holder or the like to function as a cutting tool. Such a throw-away tip is a disposable tip which is changed, rather than polished for reuse, when its cutting edge is worn out. The throw-away tip has cutting ridges provided on respective corners of a generally planar rectangular or triangular base. When one of the corner cutting ridges is worn out, another of the corner cutting ridges is used. Then, the throw-away tip is changed when all the corner cutting ridges are worn out.

However, it is not easy to check how far the cutting ridges of the throw-away tip have been worn. In view of an operating environment, it is particularly difficult to detect the abrasion degree of a cutting ridge currently used for cutting without interrupting the cutting process.

Conventional methods for detecting the abrasion degree of the cutting ridge are as follows:

(1) The cutting process is interrupted, and the throw-away tip is removed from the holder to be observed the cutting ridge by means of a tool microscope or the like.

(2) The abrasion degree of the cutting ridge is estimated by detecting a phenomenon incidental to the abrasion of the cutting ridge. For example, a reduction in cutting ability, an increase in vibration, occurrence of a noise, or the like is detected by a sensor disposed adjacent a working portion on a machine tool, and the estimation of the abrasion degree is based on a detection signal from the sensor.

In the method (1), however, the cutting process is interrupted, and the abrasion degree of the cutting ridge cannot quantitatively be determined, so that the abrasion detection cannot accurately be performed.

The method (2) requires a complicated detector, and is less reliable with a poor sensitivity for the detection of the abrasion degree.

One approach to these problems is described in Japanese Unexamined Utility Model Publication No. 3-120323 (1991). This publication discloses a throw-away tip having a sensor line of a conductive film provided along a cutting ridge on a flank thereof. It is also disclosed that the sensor line has a width conforming to an allowable abrasion width. In accordance with the throw-away tip disclosed in the publication, the sensor line is worn as the cutting ridge is worn, so that expiration of the life of the cutting ridge can be detected when the sensor line is cut off.

Further, Japanese Unexamined Patent Publication No. 9-38846 (1997) proposes an ordinary cutting tool (not a throw-away tip) which has a thin film circuit on a flank thereof, wherein expiration of the life of the cutting tool is automatically detected by sensing a change in electrical resistance which occurs due to abrasion of the thin film circuit as the flank is worn.

When a sensor line is provided on the throw-away tip described above, as shown in FIG. 21, an unnecessary pattern portion (solidly shaded areas in FIG. 21) is removed by irradiating a beam of laser. In order to provide a sensor line 12 on a flank 8, however, it is necessary to irradiate a beam of laser also to a cutting edge 9 portion used in the cutting process, and for this reason, the irradiated cutting edge 9 portion melts and turns into solid solution again, which undesirably makes a rough surface.

The cutting process is performed by setting cutting feed per revolution, and for example, given 0.2 mm as the feed per revolution, then, cutting resistance is applied on a rake face 5 side 0.2 mm inside from the ridge between the flank 8 and rake face 5. Because a beam of laser is irradiated to a portion where the load is applied, the surface on that portion is made rough, which reduces the cutting strength and causes a minute crack on the cutting edge 9 portion during the cutting operation. Performing the cutting process under such a condition poses a problem that chipping is induced. Also, the occurrence of a minute crack on the cutting edge 9 portion poses a problem that the finishing surface of a workpiece is made rough.

SUMMARY OF THE INVENTION

It is therefore an object of the present invention to provide a throw-away tip capable of solving the above problems, and on which a sensor line can be provided without making a rough surface of a cutting edge portion.

Another object of the present invention is to provide a throw-away tip, which eliminates inconveniences caused when the sensor line is provided that chipping readily occurs on the cutting edge portion.

A throw-away tip of the present invention has a rake face formed on a surface of a base and a flank intersecting with the rake face. The intersection ridge between the rake face and flank defines a cutting edge. A sensor line is made out of a conductive film extending along the cutting edge and having a predetermined width. The sensor line is provided in an electrically insulative relation with respect to the base. According to the present invention, one side edge of the sensor line is provided on the flank substantially in parallel with the intersection ridge, while the other side edge of the sensor line is provided on the rake face side from the intersection ridge.

In other words, according to the present invention, the sensor line is provided mainly on the flank along the cutting edge, and partially on the rake face side astride the cutting edge, whereby a narrow region parallel to the cutting edge is formed on the rake face side.

The above arrangement makes it unnecessary to irradiate a beam of laser onto the cutting edge itself when the sensor line is formed by irradiating a beam of laser. Consequently, inconveniences such that the cutting edge becomes rough, a minute crack occurs on the cutting edge, etc. can be eliminated.

The throw-away tip is provided with a pair of contact regions electrically connectable to an external electric circuit, and one end and the other end of the sensor line are connected to these contact regions via a pair of connection lines, respectively. The pair of connection lines pass through the intersection ridge of the base, and therefore, it is preferable to recess the intersection ridge portion of the base where the connection lines pass through.

By recessing the intersection ridge portion where the connection lines pass through, it is possible to prevent the intersection ridge from colliding with a holder when the throw-away tip is attached to the holder, thereby forestalling disconnection of the connection lines passing through the intersection ridge.

The above and other objects, arrangements and advantages of the present invention will become more apparent with the following description of the preferred embodiments with reference to the accompanying drawings.

BRIEF DESCRIPTION OF DRAWINGS

FIG. 3 is an enlarged view illustrating an intersection ridge portion where connection lines pass through;

FIGS. 6A through 6C are views illustrating one example of a throw-away tip according to another embodiment of the present invention, FIG. 6A being a view illustrating a state as viewed in a plane, FIG. 6B being a view illustrating a state as viewed from a side surface, FIG. 6C being a view illustrating a state as viewed from an end surface;

FIGS. 7A and 7B are views illustrating one example of a throw-away tip according to still another embodiment of the present invention, FIG. 7A being a view illustrating a state as viewed from a circumferential surface, FIG. 7B being a view illustrating a state as viewed in a plane;

FIGS. 15A through 15D are views illustrating one example of a grooving throw-away tip, FIG. 15A being a view illustrating a state as viewed in a plane, FIG. 15B being a view as viewed from a side surface side, FIG. 15C being a view as viewed from a bottom surface, FIG. 15D being a view as viewed from an end surface side;

FIG. 16 is a schematic perspective view illustrating the grooving throw-away tip 1 shown in FIGS. 15A through 15D, which is about to be attached to a holder;

FIGS. 17A through 17C and FIGS. 18A through 18D are views illustrating other examples of contact regions 13, 14, FIGS. 17A and 18A being views as viewed from a top surface side, FIGS. 17B and 18B being views as viewed from a side surface side, FIGS. 17C and 18C being views as viewed from an end surface side, FIG. 18D being a view as viewed from a bottom surface side;

DESCRIPTION OF PREFERRED EMBODIMENTS

Figure 1A:
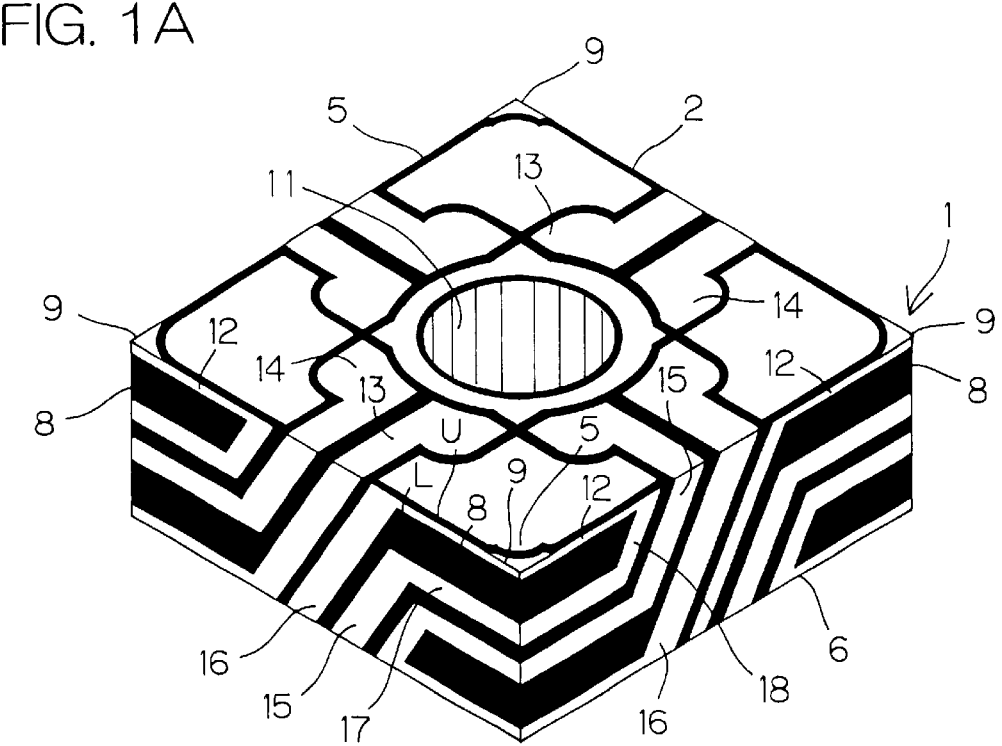
FIG. 1A is a perspective view of a throw-away tip according to one embodiment of the present invention as viewed from the upper forward side thereof.
Figure 1B:
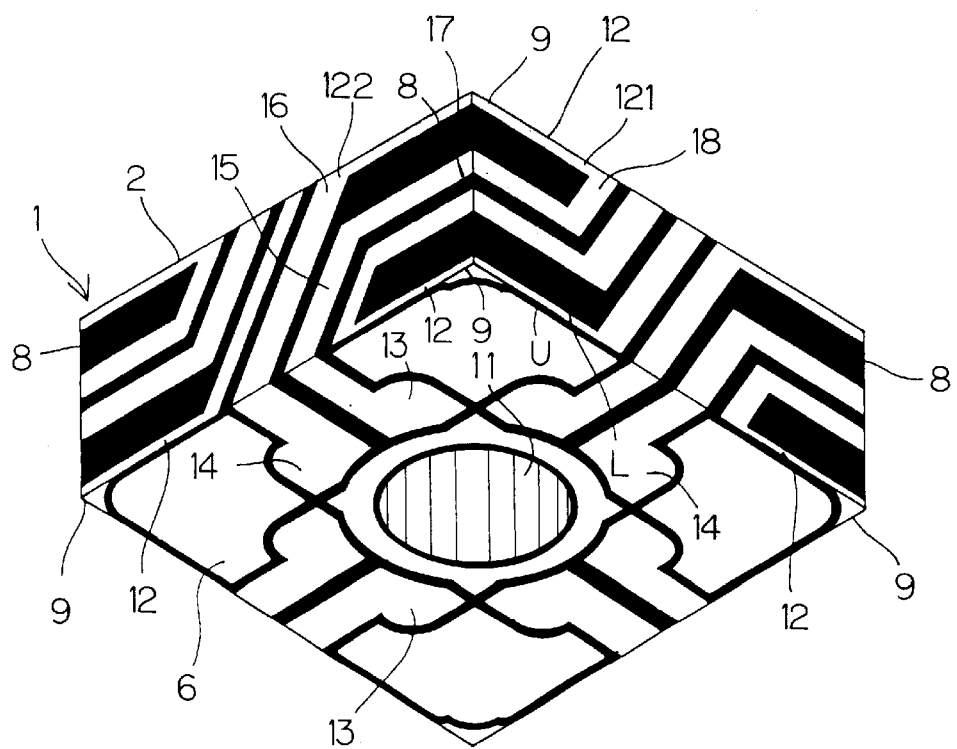
FIG. 1B is a perspective view of the throw-away tip as viewed from the lower forward side thereof.

FIG. 1A is a perspective view of a throw-away tip 1 according to one embodiment of the present invention as viewed from the upper forward side thereof, and FIG. 1B is a perspective view of the throw-away tip 1 as viewed from the lower forward side thereof. The throw-away tip 1 has a generally planar (rectangular column-shaped) base 2. For convenience of explanation, one of opposite surfaces of the base 2 is called "upper surface" and the other surface is called "lower surface", though the base 2 has no distinction between the upper and lower sides thereof.

The upper surface of the base 2 defines a rake face 5, and the lower surface of the base 2 defines a seat face 6. Four side surfaces of the base 2 respectively define flanks 8. Intersections between the rake face 5 and the respective flanks 8 define cutting ridges 9. Further, a cutting corner portion 10 is defined by an intersection between the rake face 5 and each two adjacent flanks 8.

A clamp hole 11 is formed in the center of the base 2 as extending from the upper surface to the lower surface. The throw-away tip 1 is positioned in a tip pocket of a predetermined holder and attached to the holder with the clamp hole 11 being in threading engagement with a clamp screw. With the throw-away tip thus attached, an upper forward corner portion 10 in FIG. 1A, for example, is used for cutting. By loosening the clamp screw and turning the throw-away tip 1 by 90 degrees about the clamp hole 11, another corner portion 10 can be used for cutting. By thus turning the throw-away tip 1 by 90 degrees at a time, the four corner portions 10 on the upper side can successively be used for cutting.

Further, by attaching the throw-away tip 1 to the holder in a vertically inverted manner, four corner portions on the lower side as seen in FIGS. 1A and 1B can successively be used for cutting. When any of the corner portions on the lower side is used, the upper surface serves as the seat face and the lower surface serves as the rake face. Thus, the eight corner portions 10 of the rectangular column-shaped base 2 of the throw-away tip 1 can respectively be used for cutting.

A sensor line 12 of a conductive film is provided on each of the eight corner portions 10 as extending along the cutting ridge 9.

Figure 2:
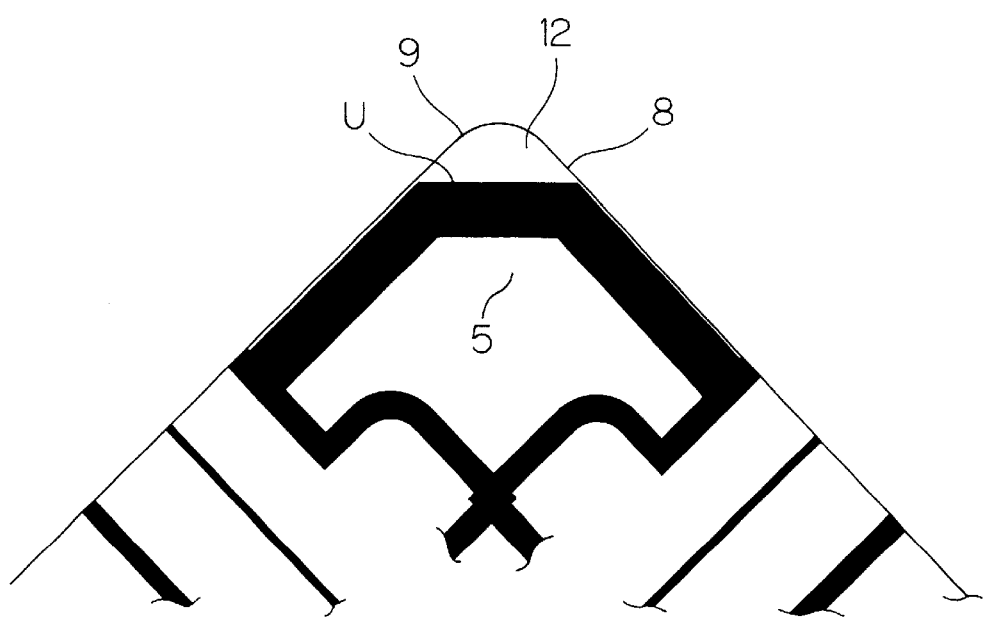
FIG. 2 is an enlarged view illustrating a cutting edge portion of the throw-away tip according to one embodiment of the present invention.

The sensor line 12 is made out of a conductive film having a predetermined width partitioned by the upper edge U and lower edge L. As is shown in an enlarged view of FIG. 2, the upper edge of the sensor line 12 at the cutting edge portion is provided on the rake face 5 side from the intersection ridge discussed above.

In the cutting process, given 0.2 mm as the feed per revolution, for example, then, cutting resistance is applied on the rake face 5 side 0.2 mm inside from the cutting ridge line of the chamfer portion of the extremity. Hence, by taking the cutting feed per revolution into consideration, the upper edge U of the sensor line 12 is patterned by irradiating a beam of laser at a portion inner from where the cutting resistance is applied.

By providing the upper edge U of the sensor line 12 at the cutting edge 9 portion on the rake face 5 side from the intersection ridge in the above manner, when the sensor line 12 is patterned by scanning a beam of laser as will be discussed below, the beam of laser will not be irradiated to the cutting edge 9 portion, thereby making it possible to prevent the surface of the cutting edge 9 portion from becoming rough upon irradiation of a beam of laser.

There is a concern that if the sensor line 12 at the cutting edge 9 portion is provided on the rake face 5 side, even when the sensor line 12 on the flank 8 side is disconnected, such disconnection cannot be confirmed because a signal passes through the sensor line 12 on the rake face 5 side. In a practical cutting process, however, scrapes are produced from the rake face 5, meaning that the sensor line 12 on the rake face 5 wears out first, and then the sensor line 12 on the flank 8 wears out. Hence, abrasion detection of the cutting edge 9 portion remains unaffected and precise.

In addition, the lower edge L of the sensor line 12 is provided on the flank 8 in parallel or almost in parallel with the intersection ridge between the rake face 5 and flank 8. In other words, the lower edge L of the sensor line 12 conforms to a reference life of a corner portion (an allowable abrasion limit of the flanks 8). The reference life of the corner portion of the throw-away tip 1 of this type is generally within a range of 0.05 to 0.7 mm, and the lower edge L of the sensor line 12 is provided at a position to have a life equal to this reference life.

For example, in case that the life expires when the abrasion on the flank 8 of the throw-away tip 1 reaches 0.2 mm, then a width W of the sensor line 12 on the flank 8 portion is set to 0.2 mm. When the cutting process is performed with the use of the corner portion, the cutting ridge 9 and flank 8 wear out with an increasing machining time. The sensor line 12 wears out in response to abrasion of the flank 8. When the abrasion width of the flank 8 reaches or exceeds the reference life, the sensor line 12 having the lower edge L conforming to the reference life is disconnected by abrasion. Because a resistance value across the sensor line 12 is measured by an external circuit as will be discussed below, expiration of the life of the cutting ridge 9 at the corner portion can be detected the instant the resistance of the sensor line 12 reaches an infinite value.

As shown in FIG. 1B, pairs of contact regions 13, 14 are provided on the seat face 6. The pairs of contact regions 13, 14 are composed of a conductive film, and insulated from the base 2. The contact regions 13, 14 are electrically connectable to an external resistance detection circuit, for example, provided outside the holder. As will be described later, the contact regions 13, 14 in each pair are electrically connected to probes of the detection circuit provided on a tip seat of the holder when the throw-away tip 1 is attached to the holder.

Pairs of connection lines 15, 16 of a conductive film are provided in an electrically insulative relation with respect to the base 2 as extending from the flanks 8 to the seat face 6 of the base 2. The connection line 15 in each pair electrically connects one end 121 of the sensor line 12 to one 13 of the contact regions, while the connection line 16 in each pair electrically connects the other end 122 of the sensor line 12 to the other contact region 14.

The connection line 15 connected to the other end 122 of the sensor line 12 includes a return line 17 as a part thereof. The return line 17 is connected to the other end 122 of the sensor line 12 at a return portion 18 thereof. The return line 17 is spaced a predetermined distance D from the sensor line 12 in a parallel relation to the sensor line 12. The provision of the return line 17 as a part of the connection line 16 makes it possible to arrange the connection lines 15, 16 in a parallel and spaced relation on the flanks 8, so that the connection lines 15, 16 can advantageously be arranged in a highly area-efficient manner.

The pair of connection lines 15, 16 formed on the flanks 8 are inclined at a predetermined inclination angle with respect to the sensor line 12 (or the cutting ridge 9), rather than extend perpendicularly to the sensor line. This is because the contact regions 13, 14 provided on the seat face 6 on the lower surface and the contact regions 13, 14 provided on the upper surface are preferably arranged in the same pattern.

Figure 3:
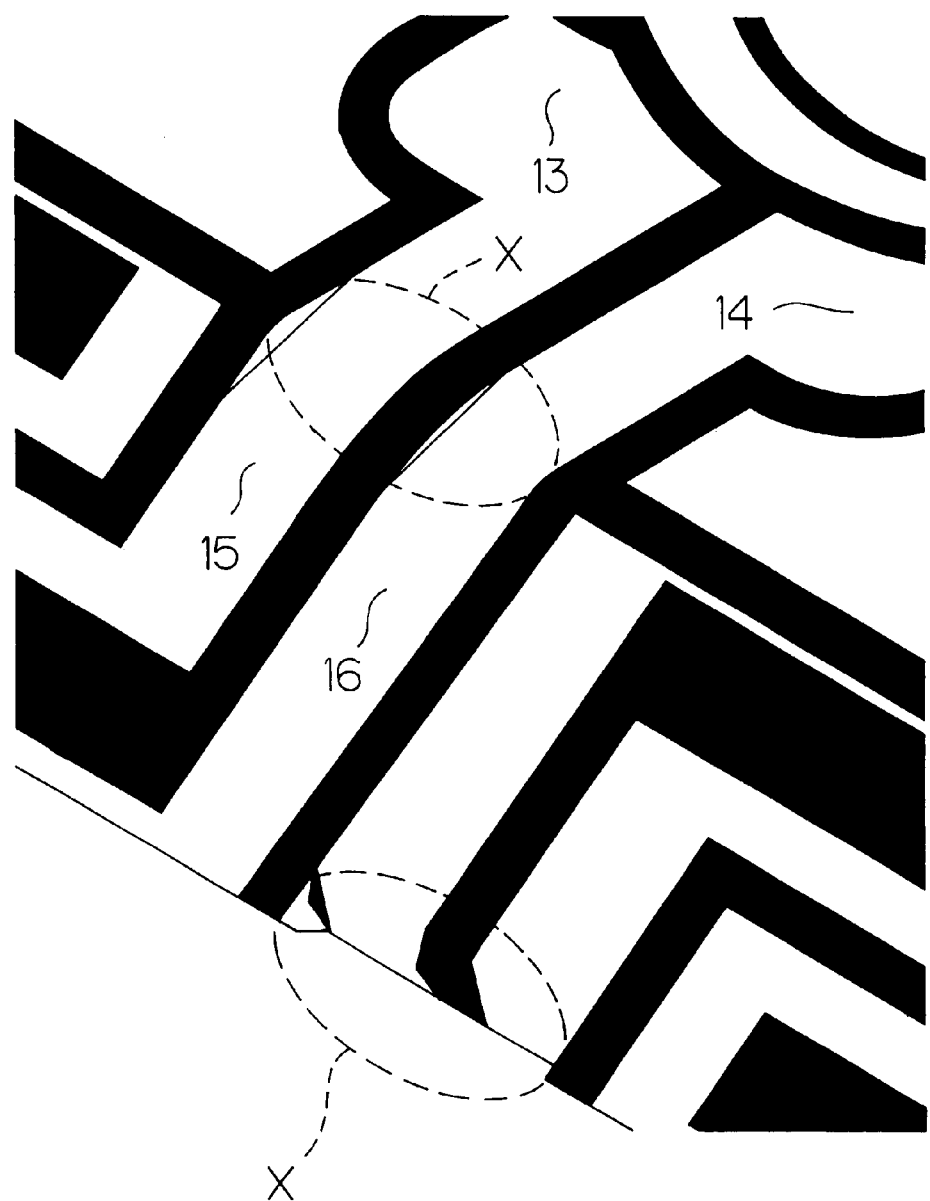

FIG. 3 is an enlarged view illustrating an intersection ridge portion where the connection lines pass through. Here, the intersection ridge portion between the side surface and one main surface or the other main surface where the connection lines 15, 16 pass through is recessed. By recessing the intersection ridge X portion between the side surface and one main surface or the other main surface where the connection lines 15, 16 pass through to form an R shape in this manner, even when the tip touches the holder or the like, the intersection ridge X portion where the connection lines 15, 16 are provided will not touch the holder, thereby making it possible to prevent disconnection of the connection lines 15, 16.

More specifically, if the intersection ridge portion between the side surface 8 and one main surface 5 or the other main surface 6 of the base 2 is sharply pointed, there occur the following problems: (1) the sharply pointed intersection ridge collides with the holder each time the tip is removed from and attached to the holder, and such collision causes the connection lines 15, 16 to be damaged and disconnected; and (2) the intersection ridge portion between the side surface 8 and one main surface 5 or the other main surface 6 of the base 2 slides over the holder when an impact is given during the cutting operation, and the connection lines 15, 16 at the intersection ridge portion are readily disconnected by abrasion. The present embodiment, however, can solve these problems.

It should be appreciated that the intersection ridge X portion only has to be recessed so as not to touch the holder as much as possible, and is not necessarily recessed in an R shape. The intersection ridge X portion can be recessed to form a C-shaped surface or recessed stepwise.

Figure 4:
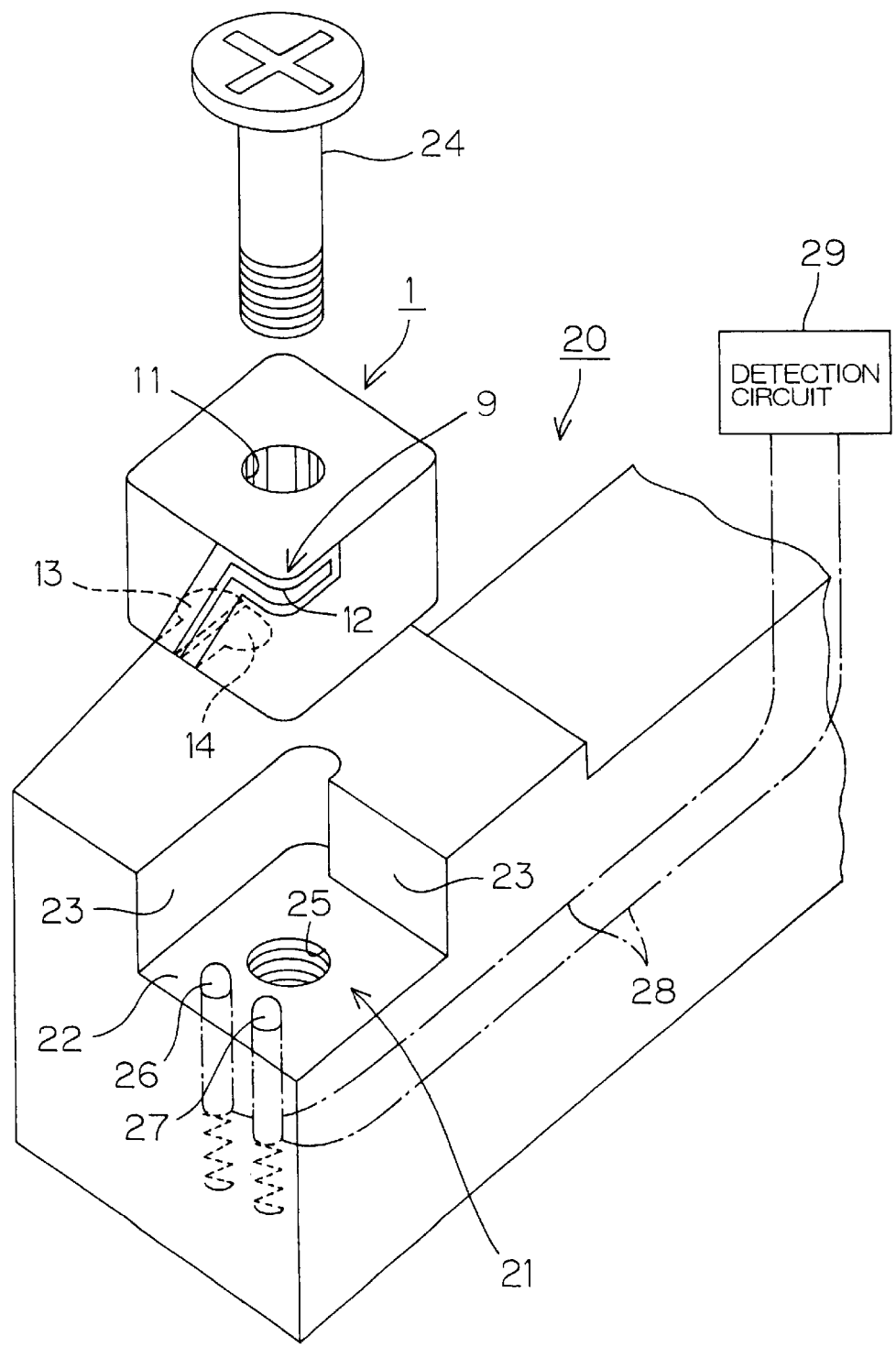
FIG. 4 is a schematic perspective view illustrating the throw-away tip 1 shown in FIGS. 1A and 1B, which is about to be attached to a holder.

FIG. 4 is a schematic perspective view illustrating the throw-away tip 1 shown in FIGS. 1A and 1B, which is about to be attached to a holder.

A tip attachment pocket 21 is provided in a distal end portion of the holder 20. A bottom surface of the pocket 21 serves as a tip seat 22. Side walls of the pocket 21 are adapted to abut against side faces of the tip to serve as restriction faces 23 for restricting the tip. The throw-away tip 1 is accommodated in the pocket 21 with the seat face 6 thereof abutting against the tip seat 22 and with the side faces abutting against the restriction faces 23. A clamp screw 24 is inserted into the clamp hole 11 of the throw-away tip 1 from the upper side, and a distal end portion of the clamp screw is brought into threading engagement with a screw hole 25 formed in the center of the tip seat 22. Thus, the throw-away tip 1 is attached to the holder 20.

A pair of probes 26, 27 project from the tip seat 22 in positions opposed to the contact regions 13, 14 connected to the sensor line 12 of the corner portion of the attached throw-away tip 1 to be used for cutting. The probes 26, 27 are resiliently biased upward to project from the tip seat 22, for example, by several millimeters. When the throw-away tip 1 is mounted in the pocket 21, the probes 26, 27 are pressed down by the seat face 6 of the throw-away tip 1, so that the upper ends of the probes are flush with the tip seat 22. Thus, the upper ends of the probes 26, 27 are brought into electrical contact with the contact regions 13, 14, respectively, on the seat face 6 of the throw-away tip 1.

The probes 26, 27 are connected to lead wires 28 provided in the holder 20 as indicated by one-dot-and-dash lines, and the lead wires 28 are connected to a resistance detection circuit 29 such as an ohm meter.

With the throw-away tip 1 mounted in the pocket 21, the resistance of the sensor line 12 provided on the corner portion 10 currently used for cutting can be measured by means of the detection circuit 29.

An explanation will next be given to materials and formation methods for the base, the sensor lines, the contact regions, the connection lines and the like of the throw-away tip according to the present invention.

Exemplary materials for the base of the throw-away tip include sintered alumina based materials, sintered silicon nitride based material, cermets, cemented carbides, sintered cubic boron nitride (cBN) based materials and sintered polycrystalline diamond (PCD) based materials.

A sintered alumina based material to be herein employed consists essentially of 2 to 30 wt % of $ZrO_2$, 0.01 to 5 wt % of at least one selected from oxides of Fe, Ni and Co, the balance $Al_2O_3$ and inevitable impurities.

A sintered silicon nitride based material to be herein employed consist essentially of 85 to 95 mol % of silicon nitride, 1 to 5 mol % of an element of the Group IIIa in the periodic table on an oxide basis, and 3 to 10 mol % impurity oxygen on an $SiO_2$ basis with an aluminum compound being present in a proportion of not greater than 1 wt % on an oxide ($Al_2O_3$) basis.

A cermet to be herein employed is a TiCN cermet, a compact which comprises 70 to 90 wt % of a hard phase component consisting essentially of 50 to 80 wt % of Ti on a carbide, nitride or carbonitride basis and 10 to 40 wt % of an element of the Group VIa in the Periodic Table on a carbide basis and having an atomic ratio (nitrogen/carbon+nitrogen) of 0.4 to 0.6, and 10 to 30 wt % of a binder phase component consisting essentially of an iron group metal.

A cemented carbide to be herein employed comprises a hard phase and a binder phase. The hard phase consists essentially of tungsten carbide, or tungsten carbide of 5 to 15 wt % of which is replaced with at least one of carbides, nitrides and carbonitrides of metals of the Group VIa, Va and VIa in the Periodic Table. Where a component other than tungsten carbide is blended, the hard phase comprises a WC phase and a solid solution phase of a composite carbide or a solid solution phase of a composite nitride. The binder phase consists essentially of an iron group metal such as Co, which is present in a proportion of 5 to 15 wt % based on the total binder phase.

The sensor line 12 to be formed on the edge portion of the throw-away tip has a predetermined electrical resistance. A change in the electrical resistance is measured by means of an ohm meter to detect the abrasion and chipping of the throw-away tip.

Examples of a material for the sensor line 12 includes: metallic materials including metals of the Groups IVa, Va and VIa such as Ti, Zr, V, Nb, Ta, Cr, Mo and W, iron group metals such as Co, Ni and Fe, and Al; carbides, nitrides and carbonitrides of the metals of the Groups IVa, Va and VIa such as TiC, VC, NbC, TaC, $Cr_3C_2$, $MO_2C$, WC, $W_2C$, TiN, VN, NbN, TaN, CrN, TiCN, VCN, NbCN, TaCN and CrCN; and (Ti,Al)N.

Among these materials, TiN is preferable for the following reasons. TiN has good adhesion to the base of the throw-away tip. TiN is nonreactive with a workpiece and the sensor lines of TiN constantly exhibit a predetermined electrical resistance, so that the abrasion and chipping of the throw-away tip can accurately be detected. TiN effectively prevents a work surface of a workpiece from being scratched by a reaction product thereof. TiN has an excellent acid resistance, so that the electrical resistance of the sensor lines is hardly changed by generation of an oxide. Therefore, the abrasion and chipping of the throw-away tip can accurately be detected.

The sensor line 12 is formed in the following manner. A conductive film of a predetermined thickness is formed on the flanks of the base of the throw-away tip by a CVD method, a PVD method such as ion plating, sputtering or evaporation, or a plating method. Thereafter, the conductive film is patterned into a predetermined configuration by laser machining or etching.

If the conductive film is thin with a thickness of less than 0.05 μm, the adhesion of the conductive film to the surface of the base is poor and the electrical resistance of the sensor line 12 is increased, so that it may be difficult to accurately detect the abrasion and chipping of the throw-away tip. If a conductive film having a thickness of greater than 20 μm is to be formed, a great internal stress occurs inside the conductive film at the formation thereof, whereby the conductive film may have poor adhesion to the surface of the base.

The conductive film of TiN, (Ti,Al)N, (Ti,Al)CN or the like formed on the surface of the base of the throw-away tip is patterned into a predetermined configuration for formation of the sensor line 12, the contact regions 13, 14, the connection lines 15, 16 and the like by laser machining or etching. Where the laser machining is employed for the patterning, a YAG laser beam having a width of 50 μm, a wavelength of 1.06 μm and an output of 35 kHz and 10 A is scanned over the TiN film or the like formed on the surface of the base at a drawing speed of 100 to 300 mm/s. Alternatively, a $CO_2$ laser having an illumination spot diameter of 0.3 mm and an output of 20 W is scanned over the TiN film at a drawing speed of 0.3 m/min.

Where the base of the throw-away tip is composed of an insulative material such as a sintered alumina based material, a sintered silicon nitride based material or cBN, the sensor line 12 and the like are formed directly on the surface of the base. Where the base is composed of a conductive material such as a cemented carbide or a cermet, an intermediate layer of an insulative material such as alumina intervenes between the sensor line 12 and the base.

The intermediate layer of an insulative material such as alumina serves for electrical isolation of the sensor line and the like. The intermediate layer which has a predetermined thickness is formed between the surface of the base and the sensor line and the like (conductive film) by a CVD method or the like.

More specifically, where the intermediate layer is composed of alumina, the formation of the intermediate layer is achieved in the following manner. The base of the throw-away tip is placed in a reaction vessel of a heat resistant alloy which is condition at a temperature of about 1050° C. and at a pressure of 6.5 kPa. Then, $H_2$, $CO_2$ and $AlCl_3$ are introduced into the reaction vessel at flow rates of 40 to 50 l/min, 1 to 3 l/min and 0.5 to 2 l/min, respectively, for two hours to generate $Al_2O_3$, whereby the base is coated with $Al_2O_3$.

If the intermediate layer has a thickness of less than 1 μm, electrical short may occur between the base and the sensor lines, so that the abrasion and chipping of the throw-away tip cannot accurately be detected. If an intermediate layer having a thickness of greater than 10 μm is to be formed, a great internal stress occurs inside the intermediate layer at the formation thereof, whereby the intermediate layer may have poor adhesion to the surface of the base. Even with application of a small external force, the intermediate layer may readily be separated from the surface of the base. Therefore, the thickness of the intermediate layer is preferably in the range of 1 μm to 10 μm.

FIGS. 5A, 5B, 5C, 5D, and 5E are plan views and front views (front side views) illustrating various configurations of throw-away tips to which the present invention is applicable.

Figure 5A:
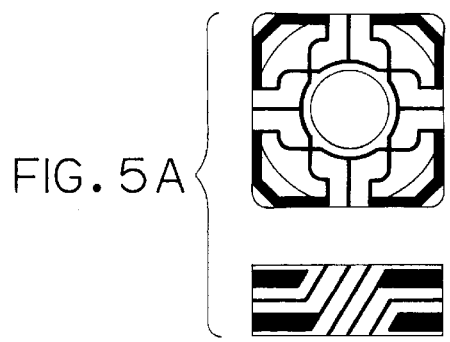
FIGS. 5A through 5E are plan views and front views illustrating various configurations of throw-away tips to which the present invention is applicable.

FIG. 5A illustrates the throw-away tip having the base of a substantially square plan shape described with reference to FIGS. 1A and 1B.

Figure 5B:
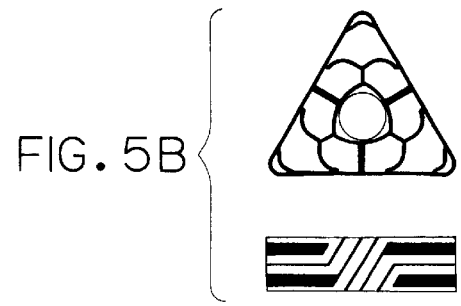

FIG. 5B illustrates a throw-away tip having a base of an equilateral triangular plan shape. The tip has three corner portions on each of the upper and lower surfaces and each can be used for cutting. More specifically, the tip has a total of six corner portions, and each is provided with the sensor line while pairs of contact regions for the respective sensor lines are provided on the seat face.

Figure 5C:
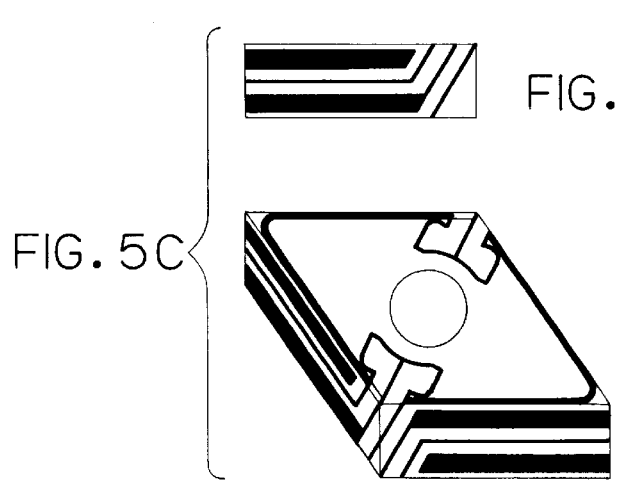

FIG. 5C illustrates a tip having a base of a rhombic plan shape. In the throw-away tip shown in FIG. 5C, two pairs of diagonally opposite acute-angle corner portions are used for cutting.

Figure 5D:
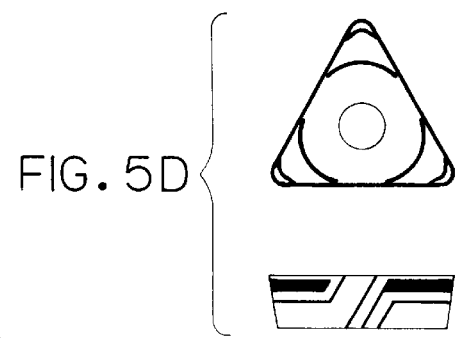

FIG. 5D illustrates a throw-away tip having a base of an equilateral triangular plan shape as the one illustrated in FIG. 5B. Different from those illustrated in FIGS. 5A through 5C, the one shown in FIG. 5D is a throw-away tip of so-called positive type, with which only one surface is used for cutting. With the tip of this type, the upper and lower surfaces serve as the rake face and seat face, respectively, and the tip cannot be used when it is upside down. Three corner portions on the upper surface are used for cutting, and therefore, each is provided with a sensor line. In addition, pairs of contact regions are provided on the lower surface serving as the seat face, and pairs of connection lines are provided on the side surfaces serving as the flanks.

Figure 5E:
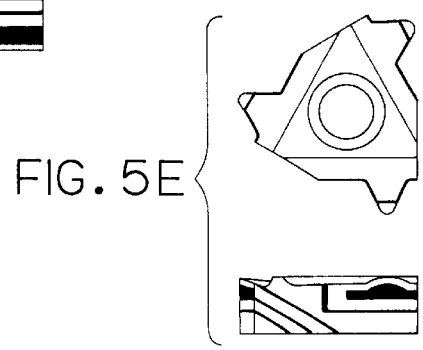

FIG. 5E illustrates a screw cutting tip having a base of a substantially triangular plan shape. The screw cutting tip is provided with a cutting edge for turning (cutting) screw grooves in the vicinity of each apex of the triangle.

Besides the foregoing configurations, the present invention is applicable, for example, to throw-away tips having a round or oval plan shape, grooving tips, etc.

In each of these tips, a sensor line made out of a conductive film having a predetermined width partitioned by the upper and lower edges is provided at the cutting edge portion in an electrically insulative relation with respect to the base, and the lower edge of the sensor line is provided on the flank in parallel or almost in parallel with the intersection ridge between the rake face and flank while the upper edge of the sensor line at the cutting edge portion is provided on the rake face side from the intersection ridge.

The inventors of the present invention conducted a cutting test. Then, with the tips provided with the sensor lines patterned by irradiating a beam of laser to the cutting edge portions in the conventional manner, chipping occurred at the cutting edge portion in as many as five tips out of one hundred. On the contrary, with the tips provided with the sensor lines having its upper edge formed on the rake face as is in the present invention, chipping occurred in none of one hundred tips.

Also, in each type of tips illustrated in FIGS. 5A through 5E, it is preferable to recess the intersection ridge portion between the side surface and one main surface or the other main surface where the connection lines pass through in an R shape.

FIGS. 6A through 6C are views illustrating one example of a throw-away tip according to another embodiment of the present invention. The throw-away tip of this type is used in a grooving process. With the throw-away tip of this type, at each end portion of a substantially column shaped tip main body 2, the top surface defines a rake face 5, the end surface defines a front flank 8a, and the side surfaces define side flanks 8b, wherein the ridge portion between the rake face 5 and front flank 8a defines a front cutting edge 9a, and the ridge portions between the rake face 5 and side flanks 8b define side cutting edges 9b.

A sensor line 12 made out of a conductive film extending along the front cutting edge 9a portion and side cutting edges 9b portions and having a predetermined width partitioned by the upper and lower edges is provided in an electrically insulative relation with respect to the base. The lower edge L of the sensor line 12 is provided on the flanks in parallel or almost in parallel with the ridge portions. The upper edge U of the sensor line 12 at the cutting edge portions 9a, 9b is provided on the rake face 5 side from the ridge portions.

With the throw-away tip of this type, one connection region 13 is provided on the top surface side of the tip main body 2, and the other connection region (not shown) is provided on the back (bottom) surface side of the tip main body 2, so that the sensor line 12 is connected to these connection regions via connection lines 15, 16, respectively.

FIGS. 7A and 7B are views illustrating one example of a throw-away tip according to still another embodiment of the present invention. The throw-away tip of this type is also used in the grooving process and the like. With the throw-away tip of this type, three pairs of a rake face 5 and a flank 8 adjacent to each other in the circumferential direction are provided on the outer circumferential surfaces of a tip main body 2 having a substantially plan shape as a whole, and the intersection position between the rake face 5 and flank 8 in each pair defines a cutting edge 9 in a thickness direction thereof.

A sensor line 12 made out of a conductive film having a predetermined width partitioned by the upper edge U and lower edge L is provided to each cutting edge 9 portion in an electrically insulative relation with respect to the base. The lower edge L of the sensor line 12 is provided on the flank 8 in parallel or almost in parallel with the intersection position. The upper edge U of the sensor line 12 at each cutting edge 9 portion is provided on the rake face 5 side from the intersection position.

With the throw-away tip of this type also, one connection region 13 is provided on the top surface side of the tip main body 2, and the other connection region (not shown) is provided on the back (bottom) surface side of the tip main body 2, so that the sensor line 12 is connected to these connection regions via connection lines 15, 16, respectively.

Figure 8A:
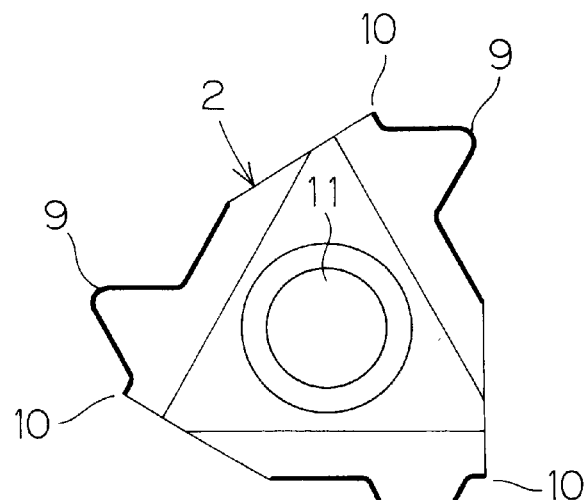
FIGS. 8A through 8C are views illustrating one example of a screw cutting throw-away tip according to still another embodiment of the present invention, FIG. 8A being a view illustrating a state of the throw-away tip as viewed in a plane, FIG. 8B being a view as viewed from a circumferential surface side, FIG. 8C being a view as viewed from a bottom surface side.
Figure 8B:
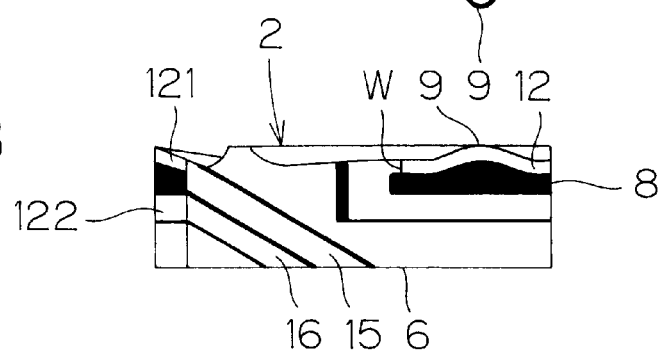
Figure 8C:
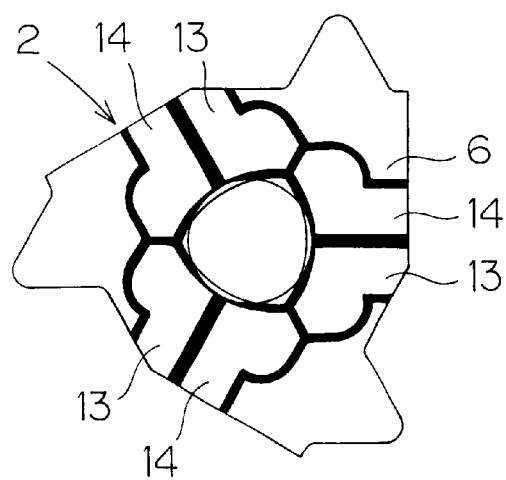

FIGS. 8A, 8B, and 8C are views illustrating a screw cutting throw-away tip according to still another embodiment of the present invention. FIG. 8A is a view illustrating a state as viewed in a plane, FIG. 8B is a view as viewed from a circumferential surface side, and FIG. 8C is a view as viewed from a bottom surface side.

A tip main body 2 is a substantially triangular plate having the top, bottom, and circumferential surfaces. Three cutting edges 9 projecting to conform to screw grooves are provided at the ridge portions between the top and circumferential surfaces in the vicinity of three apexes 10 of the tip main body 2, respectively.

The base 2 is provided with a clamp hole 11 that penetrates through from the top surface to the bottom surface at or nearly at the center. A clamp screw is inserted into the clamp hole 11, and the throw-away tip 1 is attached as it is positioned in a tip pocket, such as a predetermined holder. When attached to the holder, for example, the cutting edge 9 in the vicinity of the apex 10 at the lower right side in FIG. 8A is used for turning (cutting). Also, by loosening the clamp screw and turning the throw-away tip 1 by 120 degrees around the clamp hole 11, the cutting edge 9 in the vicinity of another apex 10 can be used for turning (cutting).

As has been discussed, with the screw cutting throw-away tip of this type, three cutting edges 9 are provided in the vicinity of three apexes 10, respectively, and by turning the tip by 120 degrees as viewed in a plane, the cutting edge 9 in the vicinity of another apex 10 can be used for turning (cutting) Hence, a sensor line 12 of a conductive film extending along the cutting edge 9 is provided on each of the circumferential surfaces (flanks) in the vicinity of the three apexes 10 of the tip main body 2.

The sensor line 12 is made out of a conductive film having a predetermined width partitioned by the upper and lower edges. The sensor line 12 is of the same structure of the example illustrated in FIGS. 1A and 1B.

As shown in FIG. 8C, three pairs of contact regions 13, 14 are provided at or nearly at the center of the bottom surface 6. Three pairs of the contact regions 13, 14 are made out of a conductive film and insulated from the main body 2. The contact regions 13, 14 in each pair are electrically connectable to a resistance detection circuit, for example, provided outside the holder. When the throw-away tip 1 is attached to the holder as will be discussed below, probes of the detection circuit provided at the seat face of the holder are electrically connected to the contact regions 13, 14. The contact regions 13, 14 preferably have as great areas as possible for easy connection to the probes of the detection circuit.

A pair of connection lines 15, 16 made out of a conductive film are provided in an electrically insulative relation with respect to the base 2 as extending from each circumferential surface 8 to the bottom surface 6. The connection line 15 electrically connects one end 121 of the sensor line 12 to the contact region 13, and the connection line 16 electrically connects the other end 122 of the sensor line 12 to the other contact region 14. The connection lines 15, 16 are lines sufficiently thicker than a width W of the sensor line 12 thereby to have an electrical resistance value sufficiently larger than that of the sensor line 12. Accordingly, the connection lines 15, 16 do not affect the detection of a change in the electrical resistance value of the sensor line.

Also, because the throw-away tip 1 can be turned by 120 degrees for use, the contact regions provided at the bottom surface as shown in FIG. 8C are symmetrically arranged in a 120-degree angularly spaced relation around the center of the top surface.

Figure 9:
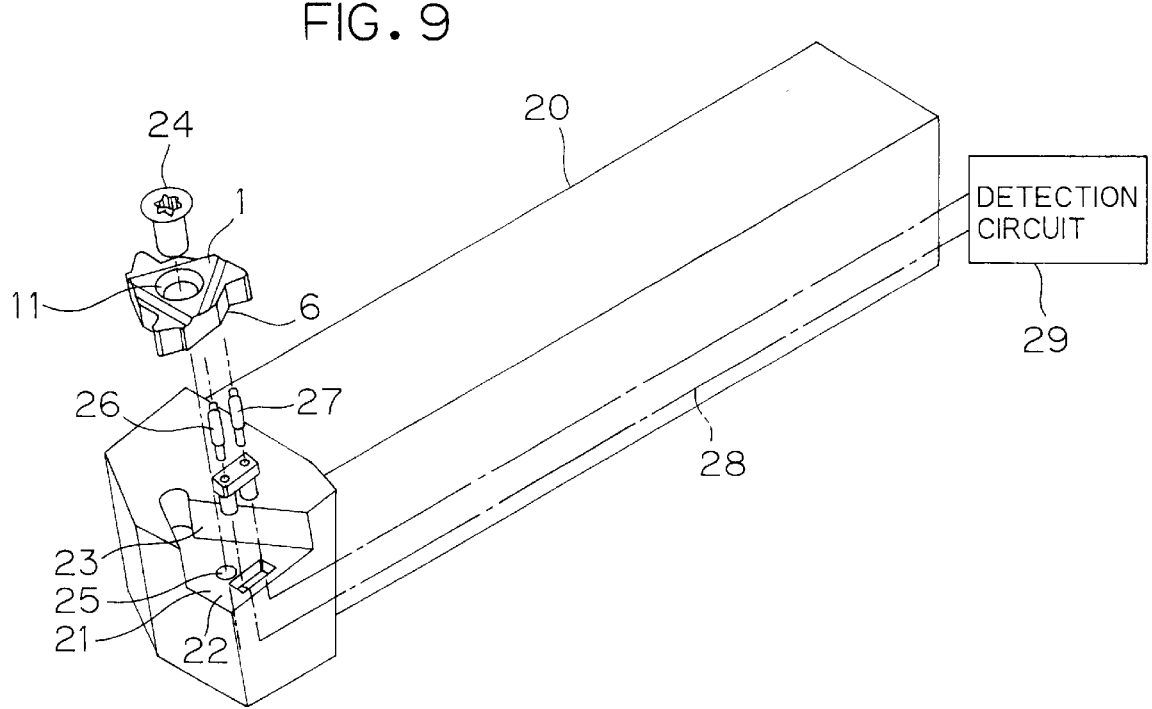
FIG. 9 is a view illustrating the screw cutting throw-away tip shown in FIGS. 8A through 8C, which is about to be attached to a holder.

FIG. 9 is a schematic perspective view illustrating the screw cutting throw-away tip 1 shown in FIGS. 8A, 8B, and 8C, which is about to be attached to the holder.

A tip attachment pocket 21 is provided at a distal end portion of a holder 20. A bottom surface of the pocket 21 serves as a tip seat 22. Also, a side surface of the pocket 21 is adapted to abut against the circumferential surface of the tip to serve as a restriction face 23 for restricting the tip. The throw-away tip 1 is accommodated in the pocket 21 with the bottom surface 6 abutting against the tip seat 22 and with the circumferential surface abutting against the restriction face 23. A clamp screw 24 is inserted into a clamp hole 11 of the throw-away tip 1 from the upper side, and its distal end portion is brought into threading engagement with a screw hole 25 made through at the center of the tip seat 22. As a result, the throw-away tip 1 is attached to the holder 20.

A pair of probes 26, 27 project from the tip seat 22 in positions respectively opposing the contact regions 13, 14 of the attached throw-away tip 1. The probes 26, 27 are resiliently biased upward to project from the tip seat 22, for example, by several millimeters. When the throw-away tip 1 is attached to the pocket 21, the probes 26, 27 are pressed down by the bottom surface 6 of the throw-away tip 1, so that the upper ends of the probes 26, 27 are flush with the tip seat 22, whereupon the upper ends of the probes 26, 27 are brought into electrical contact respectively with the contact regions 13, 14 provided on the bottom surface 6 of the throw-away tip 1.

The probes 26, 27 are connected to lead wires 28 provided in the holder 20 as indicated by one-dot-and-dash lines, and the lead wires 28 protrude from the latter end of the holder 20 so as to be connected to an external resistance detection circuit 29, such as an ohm meter.

Accordingly, in the throw-away tip 1 attached to the pocket 21, the resistance of the sensor line 12 provided at the apex 10 currently used for cutting can be measured by the detection circuit 29.

Figure 10A:
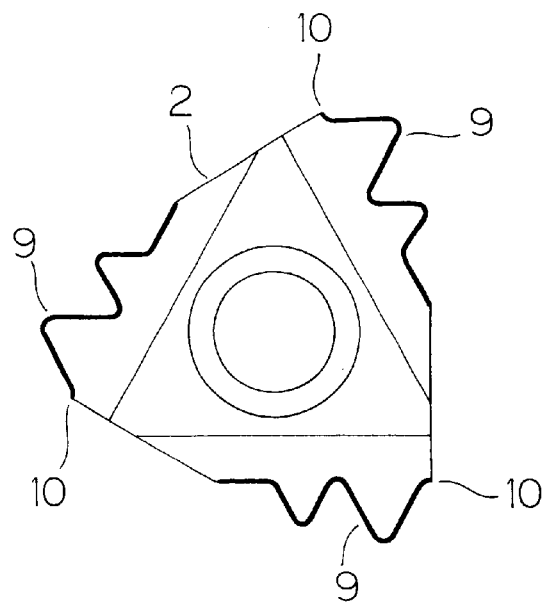
FIGS. 10A through 10C are views explaining another example of the screw cutting throw-away tip, FIG. 10A being a view illustrating a state as viewed in a plane, FIG. 10B being a view as viewed from a circumferential surface side, FIG. 10C being a view as viewed from a bottom surface side.
Figure 10B:
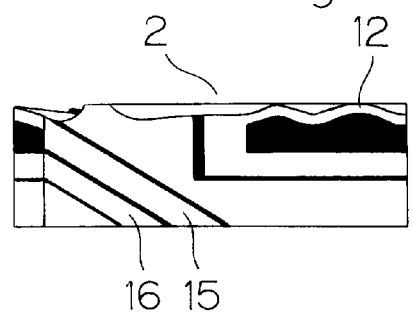
Figure 10C:
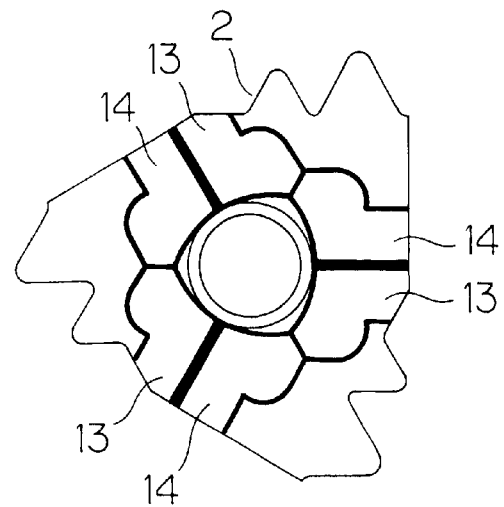

FIGS. 10A, 10B, and 10C are views illustrating another example of the screw cutting throw-away tip. FIG. 10A is a view illustrating a state as viewed in a plane, FIG. 10B is a view as viewed from a circumferential surface side, and FIG. 10C is a view as viewed from a bottom surface side. The tip main body 2 is also a substantially triangular plate having the top, bottom, and circumferential surfaces, and three cutting edges 9 each having a double profile conforming to the screw grooves are provided respectively at the ridge portions between the top and circumferential surfaces in the vicinity of three apexes 10 of the tip main body 2. The sensor line 12 can be provided to each cutting edge 9 portion protruding to shape a double profile. Besides the double profile, the cutting edge 9 may be formed in serrations, and the sensor line 12 is provided in the vicinity thereof. The sensor line 12 is of the same structure of the example illustrated in FIGS. 1A and 1B.

Figure 11A:
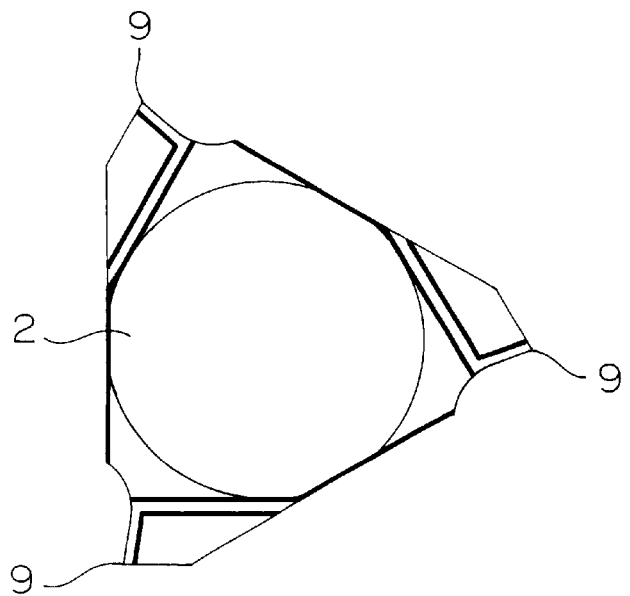
FIGS. 11A through 11C are views illustrating a further example of the screw cutting throw-away tip, FIG. 11A being a view illustrating a state of the throw-away tip as viewed in a plane, FIG. 11B being a view as viewed from a circumferential surface side, FIG. 11C being a view as viewed from a bottom surface side.
Figure 11B:
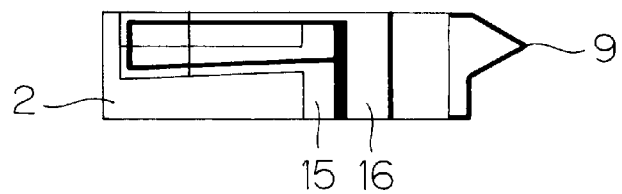
Figure 11C:
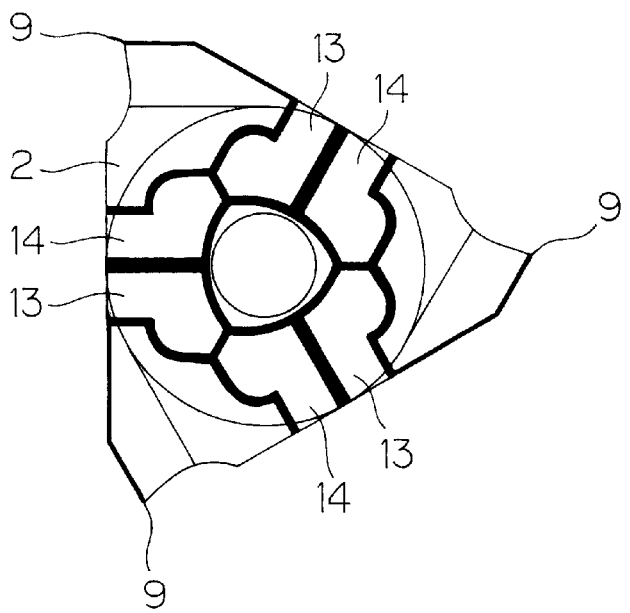

FIGS. 11A, 11B, and 11C are views illustrating a further example of the screw cutting throw-away tip. FIG. 1A is a view illustrating a state as viewed in a plane, FIG. 11B is a view as viewed from a circumferential surface side, and FIG. 11C is a view as viewed from a bottom surface side. The screw cutting throw-away tip of this type has a tip main body 2 of a polygonal plate having the top, bottom, and circumferential surfaces, and a cutting edge 9 conforming to screw grooves is provided to each apex 10 on the circumferential surfaces for turning (cutting) the screw grooves.

With the screw cutting throw-away tip of this type also, the conductive sensor line 12 extending along the cutting edge 9 on each circumferential surface of the tip main body 2 is provided in an electrically insulative relation with respect to the tip main body 2. The sensor line 12 is of the same structure of the example illustrated in FIGS. 1A and 1B.

In addition, three pairs of contact regions 13, 14 electrically connectable to a predetermined circuit are provided at the bottom surface of the tip main body 2 in an electrically insulative relation with respect to the tip main body 2. Either one of or both the contact regions 13, 14 in each pair may be provided on any of the top, bottom, or circumferential surface of the tip main body 2 or on any desired combination thereof.

A pair of connection lines 15, 16 that respectively connect the contact regions 13, 14 in each pair to one end 121 and the other end 122 of the sensor line 12 are provided on each circumferential surface of the tip main body 2 in an electrically insulative relation with respect to the tip main body 2.

Figure 12:
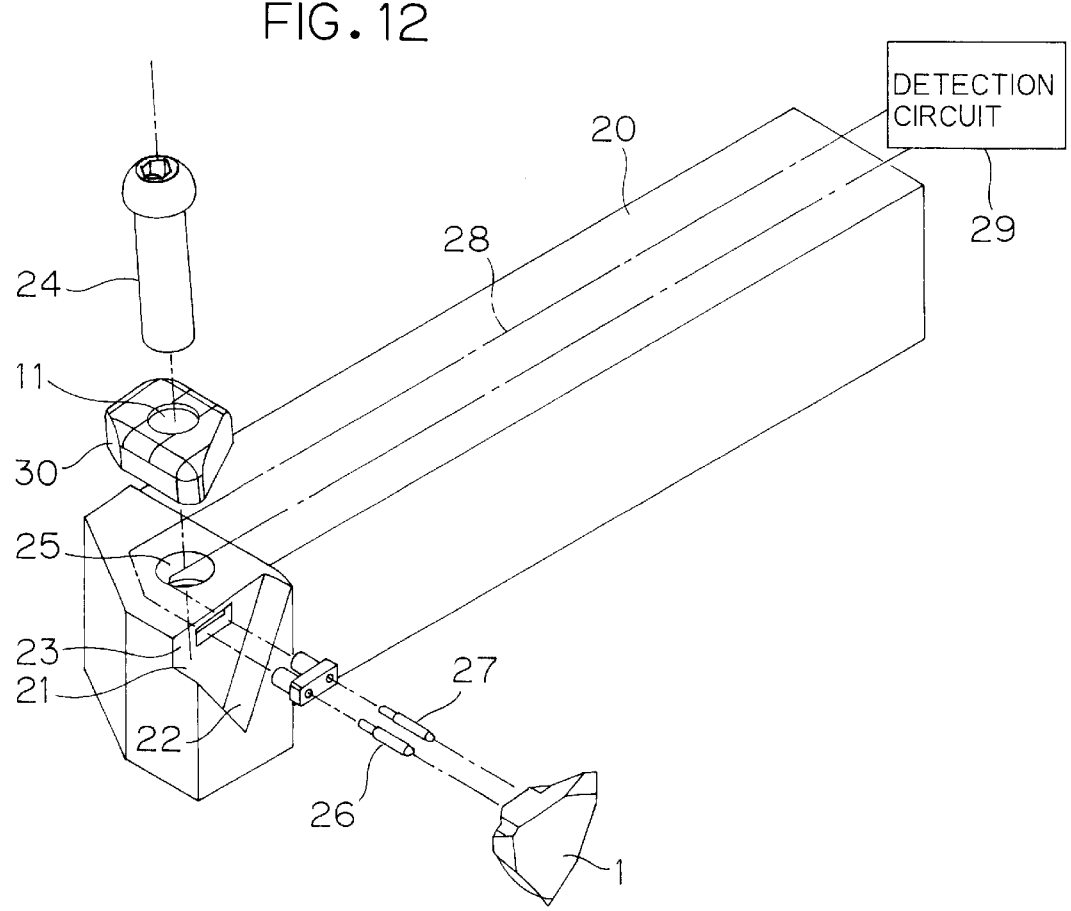
FIG. 12 is a view illustrating the screw cutting throw-away tip 1 shown in FIGS. 11A through 11C, which is about to be attached to a holder.

FIG. 12 is a view illustrating the screw cutting throw-away tip 1 shown in FIGS. 11A, 11B, and 11C, which is about to be attached to the holder.

A tip attachment pocket 21 is provided at a distal end portion of a holder 20. A bottom surface of the pocket 21 serves as a tip seat 22. Also, a side surface 23 of the pocket 21 is adapted to abut against bottom surface of the tip 1. A clamp screw 24 is inserted into a clamp hole 11 of a clamp member 30 from the upper side, and its distal end portion is brought into threading engagement with a screw hole 25 made through at the center of the tip seat 22. As a result, the throw-away tip 1 is fixed to the holder 20.

A pair of probes 26, 27 project from the side surface 23 in positions respectively opposing the contact regions 13, 14 of the attached throw-away tip 1. The probes 26, 27 are resiliently biased in a lateral direction to project from the side surface 23, for example, by several millimeters. When the throw-away tip 1 is attached to the pocket 21, the probes 26, 27 are pressed down by the bottom surface 6 of the throw-away tip 1, so that the upper ends of the probes 26, 27 are flush with the side surface 23, whereupon the upper ends of the probes 26, 27 are brought into electrical contact respectively with the contact regions 13, 14 provided on the bottom surface 6 of the throw-away tip 1.

In case that the contact regions 13, 14 are provided on the circumferential surface of the tip main body 2, the probes 26, 27 are provided to their opposing portions of the holder 20, respectively.

The probes 26, 27 are connected to lead wires 28 provided in the holder 20 as indicated by one-dot-and-dash lines, and the lead wires 28 are connected to a resistance detection circuit 29, such as an ohm meter.

Accordingly, in the throw-away tip 1 attached to the pocket 21, the resistance of the sensor line 12 provided at the apex 10 currently used for cutting can be measured by the detection circuit 29.

Figure 13:
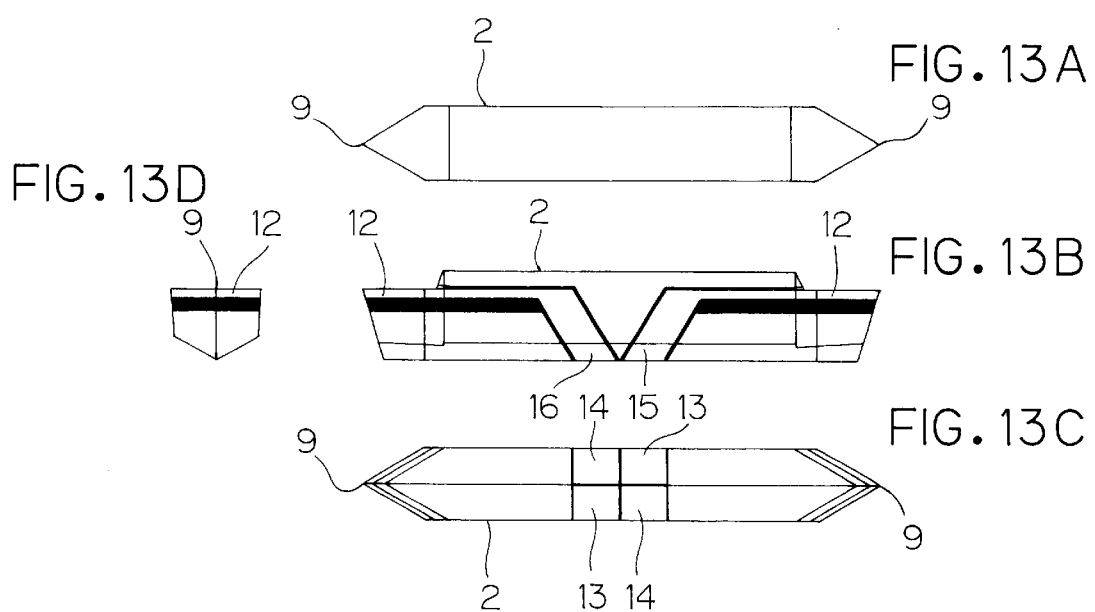
FIGS. 13A through 13D are views illustrating still another example of the screw cutting throw-away tip, FIG. 13A being a view illustrating a state of the throw-away tip as viewed in a plane, FIG. 13B being a view as viewed from a side surface side, FIG. 13C being a view as viewed from a bottom surface side, FIG. 13D being a view as viewed from an end surface side.

FIGS. 13A through 13D are views illustrating still another example of the screw cutting throw-away tip. FIG. 13A is a view illustrating a state as viewed in a plane, and FIG. 13B is a view as viewed from a side surface side. FIG. 13C is a view as viewed from a bottom surface side, and FIG. 13D is a view as viewed from an end surface side.

With the screw cutting throw-away tip of this type, at least two cutting edges 9 conforming to screw grooves are provided respectively at the both end portions of the column-wise tip main body 2 for turning (cutting) the screw grooves.

The conductive sensor line 12 of the same structure that extends along the cutting edge 9 as discussed above is provided on each end surface of the tip main body 2 in an electrically insulative relation with respect to the tip main body 2.

Two pairs of contact regions 13, 14 electrically connectable to a predetermined circuit are provided on the bottom surface of the tip main body 2 in an electrically insulative relation with respect to the tip main body 2. Either one of or both the contact regions 13, 14 in each pair may be provided on the top, bottom, or side surface of the tip main body 2, or on any desired combination thereof.

A pair of connection lines 15, 16 that respectively connect the contact regions 13, 14 in each pair to one end 121 and the other end 122 of the sensor line 12 are provided on the surface of the tip main body 2 in an electrically insulative relation with respect to the tip main body 2.

Figure 14:
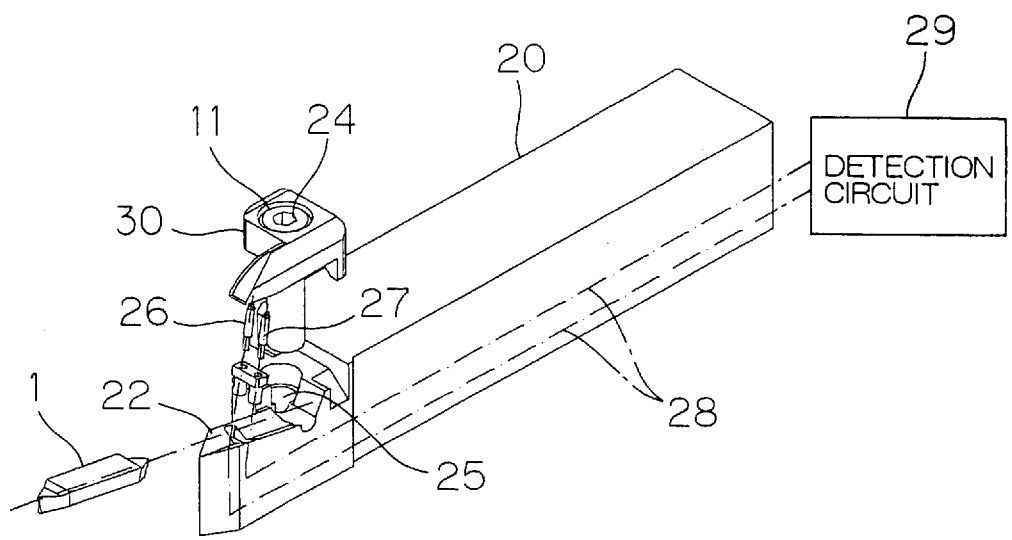
FIG. 14 is a view illustrating the screw cutting throw-away tip 1 shown in FIGS. 13A through 13D, which is about to be attached to a holder.

FIG. 14 is a view illustrating the screw cutting throw-away tip 1 shown in FIGS. 13A through 13D, which is about to be attached to a holder.

A tip attachment tip seat 22 is provided at a distal end portion of a holder 20. The throw-away tip 1 is mounted on the tip seat 22 and a clamp screw 24 is inserted into a clamp hole 11 of a clamp member 30 from the upper side, and its distal end portion is brought into threading engagement with a screw hole 25 made through in the vicinity of the tip seat 22. As a result, the throw-away tip 1 is fixed to the holder 20.

A pair of probes 26, 27 project from the tip seat 22 in positions respectively opposing the contact regions 13, 14 of the attached throw-away tip 1. The probes 26, 27 are resiliently biased upward to project from the tip seat 22, for example, by several millimeters. When the throw-away tip 1 is attached to the tip seat 22, the probes 26, 27 are pressed down by the bottom surface 6 of the throw-away tip 1, so that the upper ends of the probes 26, 27 are flush with the tip seat 22, whereupon the upper ends of the probes 26, 27 are brought into electrical contact respectively with the contact regions 13, 14 provided on the bottom surface 6 of the throw-away tip 1.

In case that the contact regions 13, 14 are provided on the top or side surface of the tip main body 2, the probes 26, 27 are provided to their opposing portions of the holder 20, respectively.

The probes 26, 27 are connected to lead wires 28 provided in the holder 20 as indicated by one-dot-and-dash lines, and the lead wires 28 are connected to a resistance detection circuit 29, such as an ohm meter.

Accordingly, in the throw-away tip 1 attached to the tip seat 22, the resistance of the sensor line 12 provided at the end portion currently used for cutting can be measured by the detection circuit 29.

FIGS. 15A through 15D are views illustrating one example of a grooving throw-away tip. FIG. 15A is a view illustrating a state as viewed in a plane, and FIG. 15B is a view as viewed from a side surface side. FIG. 15C is a view as viewed from a bottom surface, and FIG. 15D is a view as viewed from an end surface side.

The tip main body 2 has a substantially column-wise shape as a whole, and the upper side of one end portion defines a rake face 5. Also, the end surface of one end portion defines a front flank 8a, and side end surfaces define side flanks 8b, wherein the ridge portion between the rake face 5 and front flank 8a defines a front cutting edge 9a and the ridge portions between the rake face 5 and side flanks 8b define side cutting edges 9b. In addition, the front cutting edge 9a and side cutting edges 9b are defined at the other end portion of the tip main body 2.

With the grooving throw-away tip of this type, the tip main body 2 is attached to a holder through a clamp member.

The grooving throw-away tip of this type is formed to be almost horizontally symmetrical as viewed in a plane and from the side surface, and when it is turned by 180 degrees as viewed in a plane, the cutting edges 9a, 9b at the other end portion can be used for cutting. The sensor line 12 of a conductive film extending along the front cutting edge 9a and side cutting edges 9b is provided at each end portion.

The sensor line 12 is of the same structure discussed in the above examples, and the upper edge thereof is positioned on the rake face 5 side.

As shown in FIG. 15A, a contact region 13 is provided at or nearly at the center of the top surface side, and the other contact region 14 is provided at or nearly at the center of the back (bottom) surface side. These two contact regions 13, 14 are made out of a conductive film and insulated from the main body 2. The contact regions 13, 14 are electrically connectable to a resistance detection circuit, for example, provided outside the holder. When the throw-away tip 1 is attached to the holder as will be discussed below, probes of the detection circuit provided to the holder are electrically connected to the contact regions 13, 14. The contact regions 13, 14 preferably have as great areas as possible for easy connection to the probes of the detection circuit.

Connection lines 15, 16 made out of a conductive film are provided in an electrically insulative relation with respect to the base 2 as extending from the side flank 8b to the top surface side of the main body 2. The connection line 15 electrically connects one end 121 of the sensor line 12 to the contact region 13, and the connection line 16 electrically connects the other end 122 of the sensor line 12 to the other contact region 14. The connection lines 15, 16 are lines sufficiently thicker than a width W of the sensor line 12 thereby to have an electrical resistance value sufficiently larger than that of the sensor line 12. Accordingly, the connection lines 15, 16 do not affect the detection of a change in the electrical resistance value of the sensor line.

Also, because the grooving throw-away tip 1 of this type can be reversed left to right for use, the contact region 13 provided on the top surface as shown in FIG. 15A and the contact region 14 provided on the back (bottom) surface shown in FIG. 15C establish a positional relation that allows connection even when they are turned by 180 degrees around the center of the top surface.

FIG. 16 is a schematic perspective view illustrating the grooving throw-away tip 1 shown in FIGS. 15A through 15D, which is about to be attached to a holder.

A tip attachment tip seat 22 is provided at a distal end portion of a holder 20. The throw-away tip 1 is mounted on the tip seat 22 with the bottom surface 6 abutting against the tip seat 22. A clamp member attachment hole 25 is provided in the vicinity of the tip seat 22, so that a clamp member 24 is inserted and tightened. The clamp member 24 is inserted into the attachment hole 25 while pressing down the tip 1 from the upper side and brought into threading engagement with a screw hole made through at the center thereof. As a result, the throw-away tip 1 is attached to the holder 20.

A pair of probes 26, 27 project respectively from the tip seat 22 and clamp member 24 in positions respectively opposing the contact regions 13, 14 of the attached throw-away tip 1. The probes 26, 27 are resiliently biased toward the tip 1 to project respectively from the tip seat 22 and clamp member 24, for example, by several millimeters. When the throw-away tip 1 is attached to the tip seat 22, the probes 26, 27 are pressed down by the bottom and top surfaces of the throw-away tip 1, respectively, so that the upper ends of the probes 26, 27 are flush with the tip seat 22 and clamp member 24, respectively, whereupon the upper ends of the probes 26, 27 are brought into electrical contact respectively with the contact regions 13, 14 provided respectively on the top and bottom surfaces of the throw-away tip 1.

The probes 26, 27 are connected to lead wires 28 provided in the holder 20 as indicated by one-dot-and-dash lines, and the lead wires 28 are connected to a resistance detection circuit 29, such as an ohm meter.

Accordingly, in the throw-away tip 1 attached to the tip seat 22, the resistance of the sensor line 12 provided at the cutting edge 9 currently used for cutting can be measured by the detection circuit 29.

FIGS. 17A through 17C and FIGS. 18A through 18D are views illustrating other examples of the contact regions 13, 14. FIGS. 17A and 18A are views as viewed from a top surface side, and FIGS. 17B and 18B are views as viewed from a side surface side. FIGS. 17C and 18C are views as viewed from an end surface side, and FIG. 18D is a view as viewed from a bottom surface side.

In the grooving throw-away tip 1 shown in FIGS. 17A through 17C, two pairs of contact regions 13, 14 respectively connected to one end 121 and the other end 122 of the sensor line 12 are provided on the top surface side of the main body 2. Even when the contact regions 13, 14 and connection lines 15, 16 are provided in the manner as illustrated in the drawings, abrasion of the cutting edge 9 portion can be detected in a satisfactory manner. In this case, two probes are provided to the clamp member of the holder.

In the grooving throw-away tip 1 shown in FIGS. 18A through 18D, two pairs of contact regions 13, 14 respectively connected to one end 121 and the other end 122 of the sensor line 12 are provided on the bottom surface side of the main body 2. Even when the contact regions 13, 14 and connection lines 15, 16 are provided in the manner as illustrated in the drawings, abrasion of the cutting edge 9 portion can be detected in a satisfactory manner. In this case, two probes are provided to the tip seat of the holder.

Figure 19C:
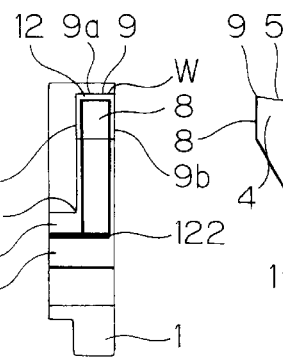
FIGS. 19A through 19C are views illustrating another example of the grooving throw-away tip, FIG. 19A being a view illustrating a state as viewed in a plane, FIG. 19B being a view as viewed from a circumferential surface side, FIG. 19C being a view as viewed from a bottom surface side.
Figure 19B:
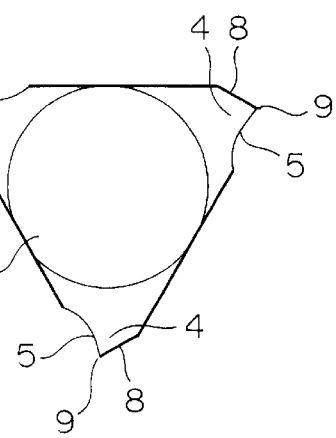
Figure 19A:
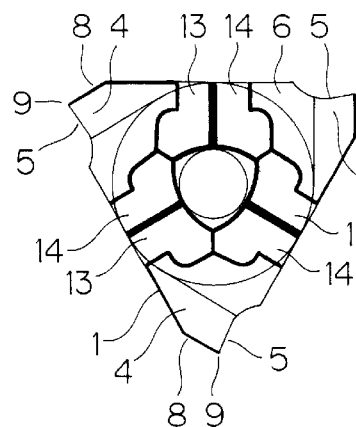

FIGS. 19A through 19C are views illustrating another example of the grooving throw-away tip. FIG. 19A is a view illustrating a state as viewed in a plane, FIG. 19B is a view as viewed from a circumferential surface side, and FIG. 19C is a view as viewed from a bottom surface side.

Three pairs of a rake face 5 and a flank 8 adjacent to each other in the circumferential direction are provided on the outer circumferential surfaces of a tip main body 2 having a substantially plan shape in a circumferential direction, and a cutting edge 9 is provided at the intersection position between the rake face 5 and flank 8 in each pair in a thickness direction thereof.

In the grooving throw-away tip of this type, three cutting edges 9 are provided in the circumferential direction, and by turning the tip 1 by 120 degrees as viewed in a plane, the cutting edge 9 at another corner portion can be used for cutting. For this reason, a sensor line 12 made out of a conductive film is provided at each of the three cutting edge 9 portions in the circumferential direction.

This sensor line 12 is made out of a conductive film having a predetermined width partitioned by the upper and lower edges, and the lower edge is provided on the flank 8 and the upper edge is provided on the rake face 5 side astride the cutting edge 9.

As shown in FIG. 19C, three pairs of contact regions 13, 14 are provided at or nearly at the center of the bottom surface 6. Three pairs of the contact regions 13, 14 are made out of a conductive film and insulated from the main body 2. The contact regions 13, 14 in each pair are electrically connectable to a resistance detection circuit provided, for example, outside the holder. When the throw-away tip 1 is attached to the holder as will be discussed below, probes of the detection circuit provided at the tip pocket of the holder are electrically connected to the contact regions 13, 14. The contract regions 13, 14 preferably have as great areas as possible for easy connection to the probes of the detection circuit.

Connection lines 15, 16 made out of a conductive film are provided in an electrically insulative relation with respect to the base 2 as extending from the flanks 8, 4 in the circumferential direction to the bottom surface 6. The connection line 15 electrically connects one end 121 of the sensor line 12 to the contact region 13, and the connection line 16 electrically connects the other end 122 of the sensor line 12 to the other contact region 14. The connection lines 15, 16 are lines sufficiently thicker than a width W of the sensor line 12 thereby to have an electrical resistance value sufficiently larger than that of the sensor line 12. Accordingly, the connection lines 15, 16 do not affect the detection of a change in the electrical resistance value of the sensor line.

Also, because the throw-away tip 1 can be turned by 120 degrees for use, the contact regions provided at the bottom surface as shown in FIG. 19C are symmetrically arranged in a 120-degree angularly spaced relation around the center of the bottom surface.

Figure 20:
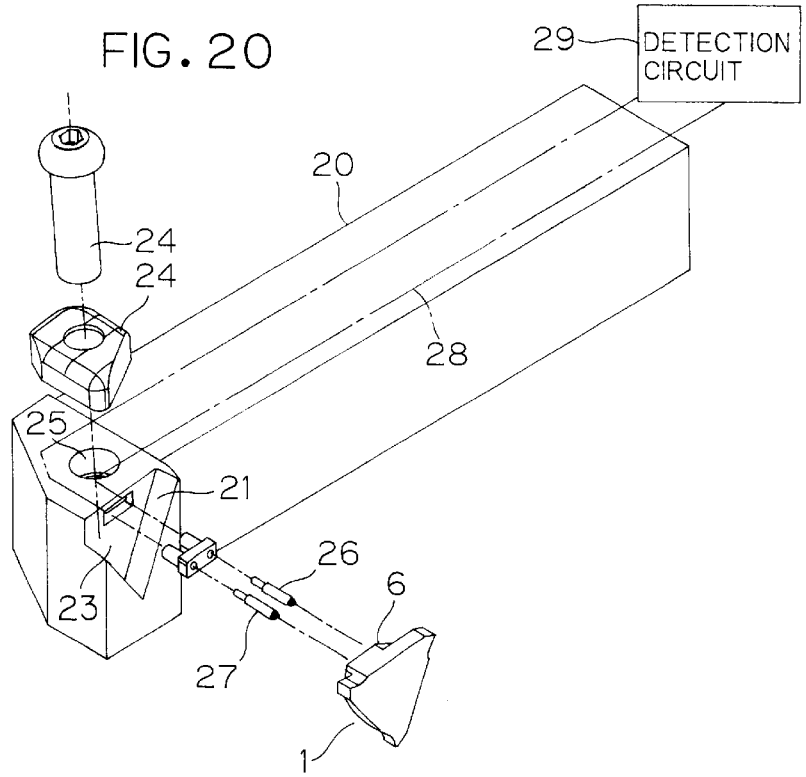
FIG. 20 is a view illustrating a method of attaching the throw-away tip shown in FIGS. 19A through 19C to a holder.
Figure 21:
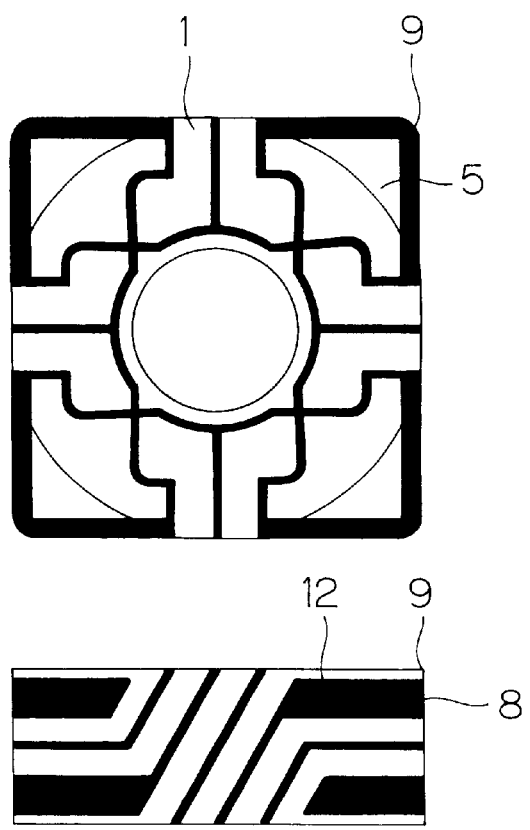
FIG. 21 is a view explaining a prior art.

FIG. 20 shows a method of attaching the throw-away tip shown in FIGS. 19A through 19C to a holder.

A tip attachment pocket 21 is provided at a distal end portion of a holder 20. The throw-away tip 1 is accommodated in the pocket 21 with the bottom surface 6 abutting against the wall surface 23 of the tip pocket 21. A clamp member attachment hole 25 is provided in the vicinity of the tip pocket 21, so that a clamp member 24 is inserted and tightened. The clamp member 24 is inserted into the attachment hole 25 while pressing down the tip 1 from the upper side and brought into threading engagement with a screw hole made through at the center thereof. As a result, the throw-away tip 1 is attached to the holder 20.

A pair of probes 26, 27 project from the side wall 23 of the tip pocket 21 in positions respectively opposing the contact regions 13, 14 of the attached throw-away tip 1. The probes 26, 27 are resiliently biased toward the tip 1 to project from the side wall 23, for example, by several millimeters. When the throw-away tip 1 is attached to the pocket 21, the probes 26, 27 are pressed down by the bottom surface 6 of the throw-away tip 1, so that the upper ends of the probes 26, 27 are flush with the side wall 23, whereupon the upper ends of the probes 26, 27 are brought into electrical contact respectively with the contact regions 13, 14 provided on the bottom surface 6 of the throw-away tip 1.

The probes 26, 27 are connected to lead wires 28 provided in the holder 20 as indicated by one-dot-and-dash lines, and the lead wires 28 are connected to a resistance detection circuit 29, such as an ohm meter.

Accordingly, in the throw-away tip 1 attached to the pocket 21, the resistance of the sensor line 12 provided at the cutting edge 9 currently used for cutting can be measured by the detection circuit 29.

With the foregoing throw-away tips, either one of or both the contact regions 13, 14 may be provided on the circumferential surface portion of the tip main body 2. In this case, the probes of the holder are provided at a V shape portion of the tip pocket 21.

What is claimed is:

1. A throw-away tip comprising:

a rake face formed on a surface of a base and a flank intersecting with said rake face, an intersection ridge between said rake face and flank defining a cutting edge, and a sensor line of a conductive film having a predetermined width defining an upper side edge and a lower side edge of said sensor line, said sensor line extending along said cutting edge in an electrically insulative relation with respect to said base, wherein said lower side edge of said sensor line is provided on said flank substantially in parallel with said intersection ridge; and wherein said upper side edge of said sensor line is provided on a side of said rake face from said intersection ridge.

2. A throw-away tip comprising:

a rake face formed on a surface of a base and a flank intersecting with said rake face, an intersection ridge between said rake face and flank defining a cutting edge, and a sensor line of a conductive film having a predetermined width and extending along said cutting edge in an electrically insulative relation with respect to said base, wherein one side edge of said sensor line is provided on said flank substantially in parallel with said intersection ridge; and the other side edge of said sensor line is provided on a side of said rake face from said intersection ridge, and wherein a pair of contact regions are provided on a surface of said base other than said flank in an electrically insulative relation with respect to said base, said contact regions being electrically connectable to an external electric circuit;

a pair of connection lines are provided on a base surface in an electrically insulative relation with respect to said base for connecting said pair of contact regions to one end and the other end of said sensor line, respectively; and an intersection ridge portion on the base surface where said connection lines pass through is recessed.

3. The throw-away tip according to claim 1, wherein:

said base has a portion of an outer surface which is substantially planar and one main surface of said base defines said rake face and a side surface intersecting with said main surface defines said flank.

4. A throw-away tip comprising:

a rake face formed on a surface of a base and a flank intersecting with said rake face, an intersection ridge between said rake face and flank defining a cutting edge, and a sensor line of a conductive film having a predetermined width and extending along said cutting edge in an electrically insulative relation with respect to said base, wherein one side edge of said sensor line is provided on said flank substantially in parallel with said intersection ridge; and the other side edge of said sensor line is provided on a side of said rake face from said intersection ridge, wherein said base has a portion of an outer surface which is substantially planar and one main surface of said base defines said rake face and a side surface intersecting with said main surface defines said flank; and said base has the other main surface opposite from said main surface;

a pair of contact regions are provided on said one main surface and/or the other main surface of said base in an electrically insulative relation with respect to said base, said contact regions being electrically connectable to an external electric circuit;

a pair of connection lines are provided in an electrically insulative relation with respect to said base as extending from said side surface to said one main surface and/or the other main surface of said base for connecting said pair of contact regions to one end and the other end of said sensor line, respectively; and an intersection ridge portion between said side surface and said one main surface and/or the other main surface of said base where said connection lines pass through is recessed.

5. The throw-away tip according to claim 4, wherein:

said portion of said outer surface of said base is polygonal and said base forms a screw cutting throw-away tip for forming a screw groove.

6. The throw-away tip according to claim 1, wherein:

said base is substantially column shaped, and a top end surface thereof defines a front flank, a side surface intersecting with said top end surface defines a side flank, and a top surface intersecting with said top end surface and side surface defines said rake face;

a front cutting edge is defined by an intersection ridge between said rake face and front flank, and a side cutting edge is defined by an intersection ridge between said rake face and side flank; and said sensor line extends along said front cutting edge and side cutting edge.

7. The throw-away tip according to claim 6, wherein:

said base has a bottom surface on a side opposite from said top surface;

a pair of contact regions are provided on said top surface and/or bottom surface of said base in an electrically insulative relation with respect to said base, said contact regions being electrically connectable to an external electric circuit;

a pair of connection lines are provided in an electrically insulative relation with respect to said base as extending from said side surface to said top surface and/or bottom surface for connecting said pair of contact regions to one end and the other end of said sensor line, respectively; and an intersection ridge portion between said side surface and said top surface and/or an intersection ridge portion between said side surface and said bottom surface where said connection lines pass through are recessed.

8. The throw-away tip according to claim 7, wherein:

said throw-away tip is a screw cutting throw-away tip having a cutting edge shaped so as to conform to a screw groove.

9. The throw-away tip according to claim 7, wherein:

said throw-away tip is a grooving throw-away tip.

10. The throw-away tip according to claim 1, wherein:

said base has a portion of its outer surface which is substantially planar and a thickness in a direction from said substantially planar portion, and a pair of said rake face and flank are provided adjacent to each other in a circumferential direction on a side surface the base; and said cutting edge is defined in said thickness direction.

11. The throw-away tip according to claim 10, wherein:

more than one pair of said rake face and flank are provided along the circumferential direction.

12. The throw-away lip according to claim 11, wherein:

said base has a top surface and a bottom surface intersecting with said side surface;

a pair of contact regions are provided on said top surface and/or bottom surface of said base in an electrically insulative relation with respect to said base, said contact regions being electrically connectable to an external electric circuit;

a pair of connection lines are provided in an electrically insulative relation with respect to said base as extending from said side surface to said top surface and/or bottom surface for connecting said pair of contact regions to one end and the other end of said sensor line, respectively; and an intersection ridge portion between said side surface and top surface and/or an intersection ridge portion between said side surface and bottom surface of said base where said connection lines pass through are recessed.

13. The throw-away tip according to claim 12, wherein:

said tip is a grooving throw-away tip.

* * * * *